United States Patent
Benson et al.

(10) Patent No.: US 10,875,873 B2
(45) Date of Patent: *Dec. 29, 2020

(54) PROCESS FOR PREPARING 2-EXO-(2-METHYLBENZYLOXY)-1-METHYL-4-ISOPROPYL-7-OXABICYCLO [2.2.1]HEPTANE

(71) Applicant: BASF Agro B.V., Arnhem (NL)

(72) Inventors: Stefan Benson, Ludwigshafen (DE); Michael Rack, Ludwigshafen (DE); Roland Goetz, Ludwigshafen (DE); Bernd Wolf, Ludwigshafen (DE); Joachim Gebhardt, Ludwigshafen (DE); Helmut Kraus, Research Triangle Park, NC (US)

(73) Assignee: BASF AGRO B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/485,563

(22) PCT Filed: Feb. 5, 2018

(86) PCT No.: PCT/EP2018/052740
§ 371 (c)(1),
(2) Date: Aug. 13, 2019

(87) PCT Pub. No.: WO2018/149676
PCT Pub. Date: Aug. 23, 2018

(65) Prior Publication Data
US 2020/0048275 A1    Feb. 13, 2020

(30) Foreign Application Priority Data

Feb. 15, 2017 (EP) ...................... 17156302

(51) Int. Cl.
*C07D 493/08* (2006.01)
(52) U.S. Cl.
CPC ................... *C07D 493/08* (2013.01)
(58) Field of Classification Search
CPC .................................................. C07D 493/08
(Continued)

(56) References Cited

U.S. PATENT DOCUMENTS

| | | | |
|---|---|---|---|
| 4,487,945 A | 12/1984 | Payne | |
| 4,542,244 A | 9/1985 | Payne et al. | |

(Continued)

FOREIGN PATENT DOCUMENTS

| | | | |
|---|---|---|---|
| CN | 101602770 | * | 5/2011 |
| EP | 0081893 A2 | | 6/1983 |

(Continued)

OTHER PUBLICATIONS

Lee et al, Metabolic Fate of Cinmethylin in Rats, J. Agric. Food Chem., 1986, 34, p. 162-170). (Year: 1986).*

(Continued)

*Primary Examiner* — Taylor V Oh
(74) *Attorney, Agent, or Firm* — Marshall, Gerstein & Borun LLP

(57) ABSTRACT

This invention relates to a process for preparing (±)-2-exo-(2-Methylbenzyloxy)-1-methyl-4-iso-propyl-7-oxabicyclo [2.2.1]heptane of the formula (I), (I) any one of its individual enantiomers or any non-racemic mixture thereof comprising the steps of (a) deprotonating (±)-2-exo-hydroxy-1-methyl-4-isopropyl-7-oxabicyclo[2.2.1]heptane of the formula (II), (II) any one of its individual enantiomers or any non-racemic mixture thereof in the presence of at least one base of the formula [Mm+]n [An-]m (III) wherein Mm+ represents a m-valent metal cation wherein m is an integer of 1 or 2, and An_ represents a n-valent anion wherein n is an integer of 1 or 2, said base being capable of forming a solvent S1 selected from water, a C1-C4 alkyl alcohol or any combination thereof under the reaction conditions, to form a metal alkoxide or metal alkoxide solvate of the formula (IV), (IV) any one of its individual enantiomers or any non-racemic mixture thereof wherein $M^{m+}$, m and the solvent S1 have the same meaning as defined for the base of formula (III), and x denotes a number from 0 to 10, and (b) reacting the metal alkoxide or metal alkoxide solvate of the formula (IV), any of its individual enantiomers or any non-racemic mixture thereof with a 2-Methylbenzyl compound of the formula (V), (V) wherein X is a leaving group, wherein the steps (a) and (b) are conducted in the presence of at least one inert organic solvent S2 and comprise a further step of (c) simultaneously removing the solvent S1 from the reaction mixture.

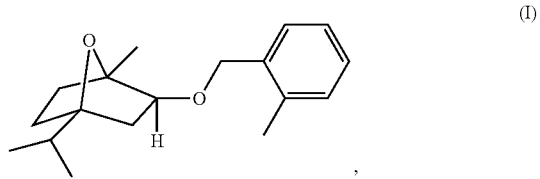

(I)

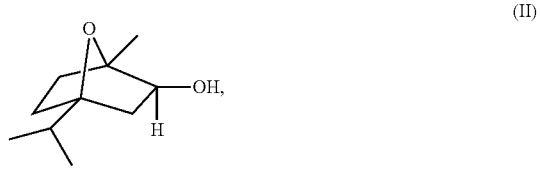

(II)

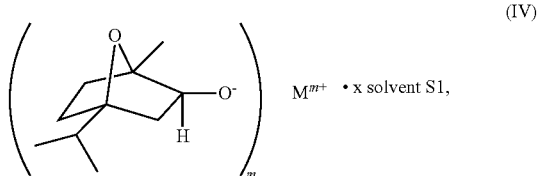

(IV)

(Continued)

-continued

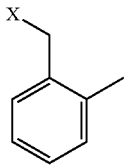

(V)

13 Claims, No Drawings

(58) Field of Classification Search
USPC .......................................................... 549/463
See application file for complete search history.

(56) References Cited

U.S. PATENT DOCUMENTS

| 4,670,041 | A | 6/1987 | Payne et al. | |
|---|---|---|---|---|
| 2020/0031792 | A1* | 1/2020 | Benson | ................ C07D 307/00 |

FOREIGN PATENT DOCUMENTS

| WO | WO-2016/180614 A1 | 11/2016 |
|---|---|---|
| WO | WO-2016/180642 A1 | 11/2016 |
| WO | WO-2017/144336 A1 | 8/2017 |
| WO | WO-2017/144337 A1 | 8/2017 |
| WO | WO-2017/215928 A1 | 12/2017 |
| WO | WO-2017/215929 A1 | 12/2017 |
| WO | WO-2018/050518 A1 | 3/2018 |

OTHER PUBLICATIONS

"The Pesticide Manual", ed. C.D.S. Tomlin, British Crop Production Council, Fourteenth Edition, 2006, pp. 195-196.
Database WPI, Thomson Scientific, London, GB; AN 2010-A51573, XP002768205, Dec. 16, 2009, 4 pages.
European Search Report for EP Application No. 17156302.6, dated Apr. 5, 2017, 3 pages.
International Search Report for PCT Patent Application No. PCT/EP2018/052740, dated Mar. 23, 2018, 4 pages.

* cited by examiner

PROCESS FOR PREPARING 2-EXO-(2-METHYLBENZYLOXY)-1-METHYL-4-ISOPROPYL-7-OXABICYCLO[2.2.1]HEPTANE

This application is a National Stage application of International Application No. PCT/EP2018/052740 filed Feb. 5, 2018. This application also claims priority under 35 U.S.C. § 119 to European Patent Application No. 17156302.6, filed Feb. 15, 2017.

This invention relates to a process for preparing (±)-2-exo-(2-Methylbenzyloxy)-1-methyl-4-isopropyl-7-oxabicyclo[2.2.1]heptane of the formula (I), any one of its individual enantiomers or any non-racemic mixture thereof by benzylating (±)-2-exo-hydroxy-1-methyl-4-isopropyl-7-oxabicyclo[2.2.1]heptane of the formula (II), any one of its individual enantiomers or any non-racemic mixture thereof with a 2-Methylbenzyl compound of the formula (V) in the presence of a base and an organic solvent wherein the compound (II) is first converted in its deprotonated form and subsequently reacted with the compound (V).

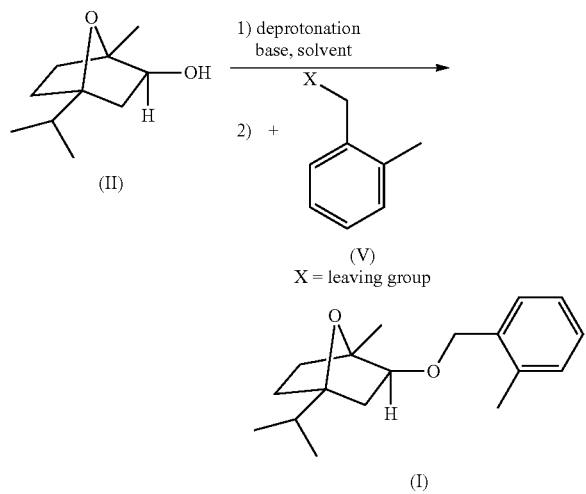

The racemic mixture (±)-2-exo-(2-Methylbenzyloxy)-1-methyl-4-isopropyl-7-oxabicyclo[2.2.1]heptane is a known herbicidal compound which has been developed for use in rice. It is described in the The Pesticide Manual, Fourteenth Edition, Editor: C. D. S. Tomlin, British Crop Production Council, 2006, entry 157, pages 195-196 with its common name Cinmethylin, its IUPAC name (1RS,2SR,4SR)-1,4-epoxy-p-menth-2-yl 2-methylbenzyl ether and its Chemical Abstracts name exo-(±)-1-methyl-4-(1-methylethyl)-2-[(2-methylphenyl)methoxy]-7-oxabicyclo[2.2.1]heptane.

The racemic mixture (±)-2-exo-(2-Methylbenzyloxy)-1-methyl-4-isopropyl-7-oxabicyclo[2.2.1]heptane (herein also referred to as the "exo-(±)-isomers", CAS RN 87818-31-3)

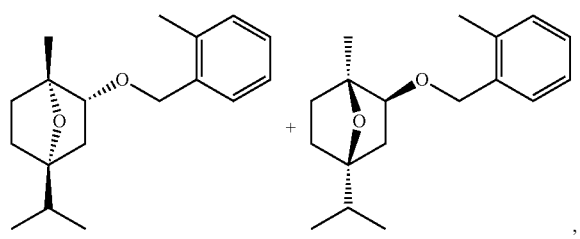

contains equal parts of the two enantiomers (+)-2-exo-(2-Methylbenzyloxy)-1-methyl-4-isopropyl-7-oxabicyclo[2.2.1]heptane (herein also referred to as the "exo-(+)-isomer", CAS RN 87818-61-9) and (−)-2-exo-(2-Methylbenzyloxy)-1-methyl-4-isopropyl-7-oxabicyclo[2.2.1]heptane (herein also referred to as the "exo-(−)-isomer", CAS RN 87819-60-1).

EP 0 081 893 A2 describes the preparation of (±)-2-exo-(2-Methylbenzyloxy)-1-methyl-4-isopropyl-7-oxabicyclo[2.2.1]heptane and its exo-(+)-isomer and exo-(−)-isomer by reacting (±)-2-exo-hydroxy-1-methyl-4-isopropyl-7-oxabicyclo[2.2.1]heptane with 2-methylbenzyl chloride in the presence of sodium hydride as a base and dimethylformamide as organic solvent (see Examples 29, 34, 35 and 62).

The use of sodium hydride as a base and dimethylformamide as organic solvent in the preparation of (±)-2-exo-(2-Methylbenzyloxy)-1-methyl-4-isopropyl-7-oxabicyclo[2.2.1]heptane by reacting (±)-2-exo-hydroxy-1-methyl-4-isopropyl-7-oxabicyclo[2.2.1]heptane with 2-methylbenzyl chloride is also described in U.S. Pat. No. 4,487,945 (see Embodiment 48), U.S. Pat. No. 4,542,244 (see Embodiment 219) and U.S. Pat. No. 4,670,041 (see Embodiment 219). Further, the preparation of the exo-(−)-isomer by reacting (−)-2-exo-hydroxy-1-methyl-4-isopropyl-7-oxabicyclo[2.2.1]heptane with 2-methylbenzyl chloride in any of the aforementioned references is conducted in the presence of sodium hydride as a base and N,N-dimethylacetamide as organic solvent (see U.S. Pat. No. 4,487,945, Embodiment 46; U.S. Pat. No. 4,542,244, Embodiment 218 and U.S. Pat. No. 4,670,041, Embodiment 218).

CN 101602770 A describes a three-step synthesis for the preparation of Cinmethylin. In steps 1 and 2, terpinen-4-ol is converted to the corresponding 1,2-epoxide which is then subjected to isomerization to give the 1,2-epoxide isomerization product. In final step 3, Cinmethylin is obtained by condensation of the 1,2-epoxide isomerization product in the presence of various combinations of bases and organic solvents (see Examples 1, 2, 3, 8 and 9: sodium hydroxide/ethyl acetate; Examples 4 and 5: sodium amide/dichloromethane; Example 6: sodium hydride/benzene and Example 7: sodium tert-butoxide/toluene).

However, alkali metal hydrides such as sodium hydride or amides such as sodium amide are dangerously reactive in the presence of small quantities of oxygen or moisture. Such reactions may lead to the formation of dangerous gases such as hydrogen ($H_2$) or ammonia ($NH_3$). Consequently, appropriate care and precautions should be exercised during handling and storage of these substances and during the aforementioned processes for preparing (±)-2-exo-(2-Methylbenzyloxy)-1-methyl-4-isopropyl-7-oxabicyclo[2.2.1]heptane. Thus, specific safety measures such as, for example, an inert gas atmosphere (e.g. nitrogen), proper cooling, removal of gases such as $H_2$ or $NH_3$ and dilution are required during the course of the reaction.

Further, alkali metal hydroxides such as sodium hydroxide are known bases in the saponification of esters. Thus, the combined use of sodium hydroxide and ethyl acetate in the synthesis of (±)-2-exo-(2-Methylbenzyloxy)-1-methyl-4-isopropyl-7-oxabicyclo[2.2.1]heptane (see Examples 1, 2, 3, 8 and 9 of CN 101602770 A) may lead to the hydrolysis of the solvent ethyl acetate. This implies the formation of relatively high amounts of undesired by-products, low yields and loss of valuable solvent which is not available for recycling.

Philip W. Lee et al., Journal of Agricultural and Food Chemistry, Vol. 34, No. 2, 1986, pages 162-170 discloses the preparation of a proposed cinmethylin metabolite, i.e. exo- 2-[[2-(Chloromethyl) phenyl]methoxy]-1-methyl-4-(1-methylethyl)-7-oxabicyclo [2.2.1] heptane, by refluxing a solution of exo-1-methyl-4-(1-methylethyl)-7-oxabicyclo-[2.2.1]heptan-2-ol] in toluene and powdered sodium hydroxide under a Stark-Dean trap until no more water was removed. The resulting solution was subsequently reacted with α,α-dichloro-o-xylene to give a ca. 50:50 mixture of the mono- and disubstitution products along with the unreacted dichloroxylene. Purification of the reaction mixture gave exo-2-[[2-(Chloromethyl) phenyl]methoxy]-1-methyl-4-(1-methylethyl)-7-oxabicyclo [2.2.1] heptane in a low yield of 30%.

The aforementioned disadvantages make the prior art processes not very suitable for an industrial scale production and unattractive for economic, environmental and working-health reasons.

In view of the above drawbacks, there is still need for an improved process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which would not only make the synthesis safe and environmentally friendly, but also would be simple and cost-effective for commercial utilization.

It is therefore an object of the present invention to overcome or ameliorate at least one of the above disadvantages and thus to provide an improved and more economically and commercially feasible process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof.

Another object is to provide an industrially simple process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which gives the desired final product in good yields.

A further object is to provide a more environmentally friendly process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, by reducing unfavorable environmental effects.

Still another object is to provide an industrially feasible process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which reduces safety concerns and the existence of hazardous conditions.

Yet another object is to provide a process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof, which reduces the formation of undesirable by-products.

It has now surprisingly been found that these and further objects are, in part or in whole, achieved by a process for preparing (±)-2-exo-(2-Methylbenzyloxy)-1-methyl-4-isopropyl-7-oxabicyclo[2.2.1]heptane of the formula (I)

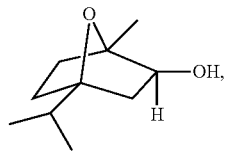

any one of its individual enantiomers or any non-racemic mixture thereof comprising the steps of (a) deprotonating (±)-2-exo-hydroxy-1-methyl-4-isopropyl-7-oxabicyclo[2.2.1]heptane of the formula (II)

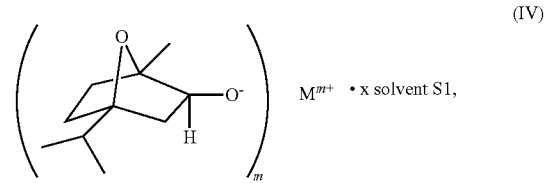

any one of its individual enantiomers or any non-racemic mixture thereof in the presence of at least one base of the formula $[M^{m+}]_n$ $[A^{n-}]_m$ (III) wherein $M^{m+}$ represents a m-valent metal cation wherein m is an integer of 1 or 2, and $A^{n-}$ represents a n-valent anion wherein n is an integer of 1 or 2, said base being capable of forming a solvent S1 selected from water, a $C_1$-$C_4$ alkyl alcohol or any combination thereof under the reaction conditions, to form a metal alkoxide or metal alkoxide solvate of the formula (IV)

any one of its individual enantiomers or any non-racemic mixture thereof wherein $M^{m+}$, m and the solvent S1 have the same meaning as defined for the base of formula (III), and x denotes a number from 0 to 10, and (b) reacting the metal alkoxide or metal alkoxide solvate of the formula (IV), any of its individual enantiomers or any non-racemic mixture thereof with a 2-Methylbenzyl compound of the formula (V)

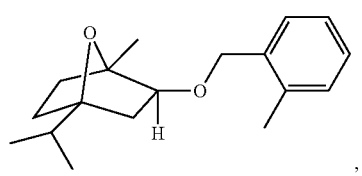

wherein X is a leaving group, wherein the steps (a) and (b) are conducted in the presence of at least one inert organic solvent S2 and comprise a further step of (c) simultaneously removing the solvent S1 from the reaction mixture.

Accordingly, the aforementioned process for the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof is a subject matter of the present invention.

The process according to the present invention entails a series of advantages and overcomes drawbacks of the prior art processes.

The process of this invention does not utilize dangerous substances such as alkali metal hydrides (e.g. sodium hydride) or amides (e.g. sodium amide) thus minimizing the existence of hazardous reaction conditions and the need for safety measures and equipment while maintaining efficiency and ease of operations.

A particular advantage of this invention is that the removal of the solvent S1 selected from water, a $C_1$-$C_4$ alkyl alcohol or any combination thereof during the reaction avoids agglomeration of salts and heavy deposits on the inner walls and various other parts of the reactor such as e.g. baffles or agitator (herein also referred to as "fouling") which would otherwise decrease the rate of conversion and lead to major difficulties on a large scale. For example, severe agglomeration of salts building up on the inner walls and other parts of the reactor may impede proper heat transfer, heat removal and agitation in the reactor. In a surprising manner, it has been found that such reactor fouling virtually does not occur in the process of this invention because salts formed during the reaction are suspended in the reaction medium as finely divided particles.

Thus, in another aspect, the present invention relates to a method for preventing or reducing the formation of deposits on the interior of a reactor in which the preparation of (±)-2-exo-(2-Methylbenzyloxy)-1-methyl-4-isopropyl-7-oxabicyclo[2.2.1]heptane of the formula (I)

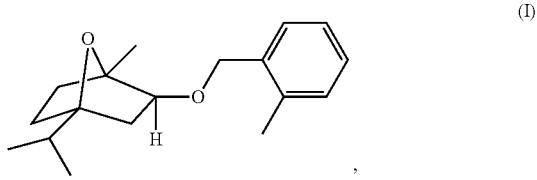 [SMILES: Cc1ccccc1COC1CC2(C(C)C)CCC1(C)O2]

(I)

any one of its individual enantiomers or any non-racemic mixture thereof is conducted by benzylating (±)-2-exo-hydroxy-1-methyl-4-isopropyl-7-oxabicyclo[2.2.1]heptane of the formula (II)

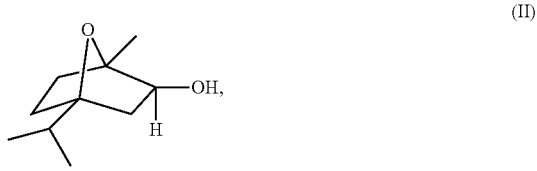

(II)

any one of its individual enantiomers or any non-racemic mixture thereof with a 2-Methylbenzyl compound of the formula (V)

(V)

wherein X is a leaving group, said method comprising the steps of (a) deprotonating (±)-2-exo-hydroxy-1-methyl-4-isopropyl-7-oxabicyclo[2.2.1]heptane of the formula (II), any one of its individual enantiomers or any non-racemic mixture thereof in the presence of at least one base of the formula $[M^{m+}]_n$ $[A^{n-}]_m$ (III) wherein $M^{m+}$ represents a covalent metal cation wherein m is an integer of 1 or 2, and $A^{n-}$ represents a n-valent anion wherein n is an integer of 1 or 2, said base being capable of forming a solvent S1 selected from water, a $C_1$-$C_4$ alkyl alcohol or any combination thereof under the reaction conditions, to form a metal alkoxide or metal alkoxide solvate of the formula (IV)

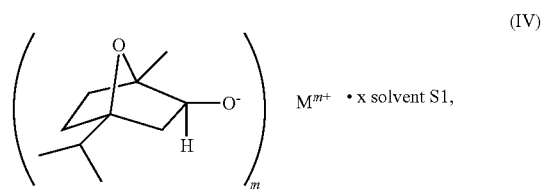

(IV)

any one of its individual enantiomers or any non-racemic mixture thereof wherein $M^{m+}$, m and the solvent S1 have the same meaning as defined for the base of formula (III), and x denotes a number from 0 to 10, and (b) reacting the metal alkoxide or metal alkoxide solvate of the formula (IV), any of its individual enantiomers or any non-racemic mixture thereof with the 2-Methylbenzyl compound of the formula (V)

wherein the steps (a) and (b) are conducted in the presence of at least one inert organic solvent S2 and comprise a further step of (c) simultaneously removing the solvent S1 from the reaction mixture.

The term "interior of a reactor" as used herein is meant to include various interior parts of a reactor such as, for example, the inner walls of a reactor, an agitator, and a baffle. In a preferred embodiment, the interior of a reactor comprises the inner walls of a reactor, an agitator, a baffle and any combination thereof and more preferably the inner walls of a reactor, an agitator or any combination thereof.

The compounds of formula (II) and (V), the base of the formula (III), the metal alkoxide or metal alkoxide solvate of the formula (IV), the solvent S1, the inert organic solvent S2 and the reaction conditions used in the aforementioned method of this invention and preferred embodiments thereof are the same as described herein for the process of this invention.

Moreover, the inert organic solvent S2 used in this invention can be recovered and recycled easily which leads to an economical and sustainable process.

Yet another advantage is that the removal of the solvent S1 selected from water, a $C_1$-$C_4$ alkyl alcohol or any combination thereof during the reaction avoids side-product formation and provides the desired (±)-2-exo-(2-Methylbenzyloxy)-1-methyl-4-isopropyl-7-oxabicyclo[2.2.1]heptane of the formula (I), any of its individual enantiomers or any non-racemic mixture thereof in high yields.

Thus, the process or method of this invention allows the preparation of (±)-2-exo-(2-Methylbenzyloxy)-1-methyl-4-isopropyl-7-oxabicyclo[2.2.1]heptane of the formula (I), any of its individual enantiomers or any non-racemic mixture thereof to proceed in a smooth and controlled manner, which is very safe, industrially simple, economical, environmentally friendly and commercially viable.

Further embodiments of the invention are evident from the claims, the description and the examples. It is to be understood that the single features of the subject matter of the invention described herein can be applied not only in the combination given in each particular case but also in other combinations, without leaving the scope of the invention.

The materials used in this invention are known compounds that are commercially available or can be prepared in a known manner.

For example, (±)-2-exo-hydroxy-1-methyl-4-isopropyl-7-oxabicyclo[2.2.1]heptane of the formula (II), any of its individual enantiomers or any non-racemic mixture thereof can be prepared by any of the methods described in EP 0 081 893 A2 (see Example 15), U.S. Pat. No. 4,487,945 (see Embodiments 1 and 45), U.S. Pat. No. 4,542,244 (see Embodiments 1 and 217) and U.S. Pat. No. 4,670,041 (see Embodiments 1 and 217) or in an analogous manner.

In the 2-Methylbenzyl compound of the formula (V), the substituent X is a leaving group. The term "leaving group" as used herein refers to any group that departs the molecule with a pair of electrons in heterolytic bond cleavage such that the molecule is capable of participating in the nucleophilic substitution reaction of the process of this invention.

Preferred leaving groups X are selected from halogen, an oxygen linked leaving group, an ammonium group of the formula (VI)

$$—N(R_1)(R_2)(R_3)^+Y^- \quad (VI)$$

wherein $R_1$, $R_2$ and $R_3$ are each independently selected from $C_1$-$C_6$-alkyl, $C_3$-$C_{10}$-cycloalkyl and $C_6$-$C_{20}$-aryl, and $Y^-$ is selected from halide, hydroxide, $C_1$-$C_4$-alkyl sulfonate and $C_6$-$C_{20}$-aryl sulfonate ions.

The organic moieties mentioned in the definition of certain variables (i.e. $R^1$, $R^2$ and $R^3$), sulfonates (i.e. $C_1$-$C_4$-alkyl sulfonates, $C_1$-$C_4$-haloalkyl sulfonates, $C_6$-$C_{20}$-aryl sulfonates and $C_3$-$C_{10}$-cycloalkyl sulfonates) and phase transfer catalysts (i.e. tetra-n-$C_1$-$C_4$-alkyl-ammonium chlorides, bromides, iodides or hydroxides, tetra-n-$C_1$-$C_8$-alkyl-ammonium chlorides, bromides, iodides or hydroxides and tetra-n-$C_1$-$C_{12}$-alkyl-ammonium chlorides, bromides, iodides or hydroxides) are—like the term halogen—collective terms for individual enumerations of the individual group members. The term "halogen" denotes in each case fluorine, chlorine, bromine or iodine. All hydrocarbon chains, e.g. alkyl chains, can be straight-chain or branched, the prefix $C_n$-$C_m$ denoting in each case the possible number of carbon atoms in the group. Examples of such meanings are:

$C_1$-$C_4$-alkyl: for example methyl, ethyl, n-propyl, iso-propyl (—CH(CH$_3$)$_2$), n-butyl, sec-butyl (—CH (CH$_3$)—C$_2$H$_5$), isobutyl (—CH$_2$—CH(CH$_3$)$_2$) or tert-butyl (—C(CH$_3$)$_3$);

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1$-$C_8$-alkyl: $C_1$-$C_6$-alkyl as mentioned above, and also, for example, n-heptyl, n-octyl or 2-ethylhexyl;

$C_1$-$C_{12}$-alkyl: $C_1$-$C_4$-alkyl as mentioned above, and also, for example, n-nonyl, iso-nonyl, n-decyl, n-undecyl or n-dodecyl;

$C_1$-$C_4$-haloalkyl: a $C_1$-$C_4$-alkyl as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl or 1-trifluoromethyl-1,2,2,2-tetrafluoroethyl; and $C_3$-$C_{10}$-cycloalkyl: for example cyclopropyl, cyclobutyl, cyclopentyl, cyclohexyl, cycloheptyl, cyclooctyl, cyclononyl or cyclodecyl.

The term "$C_6$-$C_{20}$-aryl" as used herein refers to an unsaturated aromatic carbocyclic group of from 6 to 20 carbon atoms having a single ring (e.g., phenyl) or multiple condensed (fused) rings, wherein at least one ring is aromatic (e.g. naphthalenyl or dihydrophenanthrenyl). Examples of $C_6$-$C_{20}$-aryls include phenyl, p-toluenyl, 1-naphthalenyl (1-naphthyl), 2-naphthalenyl (2-naphthyl), anthracenyl, indenyl or phenanthrenyl. A preferred aryl group is phenyl.

The term "halide ion" as used herein refers to e.g. a fluoride ion, a chloride ion, a bromide ion or an iodide ion.

Preferred oxygen linked leaving groups are selected from $C_1$-$C_4$-alkyl sulfonates, $C_1$-$C_4$-haloalkyl sulfonates, $C_6$-$C_{20}$-aryl sulfonates, $C_3$-$C_{10}$-cycloalkyl sulfonates and imidazolylsulfonate (imidazylate), more preferably from $C_1$-$C_4$-alkyl sulfonates, $C_1$-$C_4$-haloalkyl sulfonates and $C_6$-$C_{20}$-aryl sulfonates and even more preferably from $C_1$-$C_4$-alkyl sulfonates and $C_6$-$C_{20}$-aryl sulfonates.

Examples of $C_1$-$C_4$-alkyl sulfonates include but are not limited to mesylate (methanesulfonate), esylate (ethanesulfonate), n-propylsulfonate, iso-propylsulfonate, n-butylsulfonate, iso-butylsulfonate, sec-butylsulfonate and tert-butylsulfonate.

Examples of $C_1$-$C_4$-haloalkyl sulfonates include but are not limited to triflate (trifluoromethanesulfonate) and trichloromethanesulfonate.

Examples of $C_6$-$C_{20}$-aryl sulfonates include but are not limited to tosylate (p-toluenesulfonate), besylate (benzenesulfonate) and 2-naphtyl sulfonate.

Examples of $C_3$-$C_{10}$-cycloalkyl sulfonates include but are not limited to cyclohexylsulfonate.

Preferably, the oxygen linked leaving group is selected from mesylate (methanesulfonate), esylate (ethanesulfonate), n-propylsulfonate, iso-propylsulfonate, n-butylsulfonate, iso-butylsulfonate, sec-butylsulfonate, tert-butylsulfonate, triflate (trifluoromethanesulfonate), trichloromethanesulfonate, tosylate (p-toluenesulfonate), besylate (benzenesulfonate), 2-naphtyl sulfonate, cyclohexylsulfonate and imidazolylsulfonate (imidazylate), more preferably from mesylate, esylate, triflate, tosylate and besylate and even more preferably from mesylate and tosylate.

In another preferred embodiment, the leaving group X is selected from halogen, a $C_1$-$C_4$-alkyl sulfonate, a $C_6$-$C_{20}$-aryl sulfonate and an ammonium group of the formula (VI)

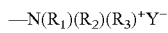

$$—N(R_1)(R_2)(R_3)^+Y^- \quad (VI)$$

wherein $R_1$, $R_2$ and $R_3$ are each independently selected from $C_1$-$C_6$-alkyl and $Y^-$ is selected from halide, hydroxide, $C_1$-$C_4$-alkyl sulfonate and $C_6$-$C_{20}$-aryl sulfonate ions.

More preferably, the leaving group X is selected from halogen, a $C_1$-$C_4$-alkyl sulfonate, a $C_6$-$C_{20}$-aryl sulfonate and an ammonium group of the formula (VI) wherein $R_1$, $R_2$ and $R_3$ are each independently selected from $C_1$-$C_6$-alkyl and $Y^-$ is selected from a halide, hydroxide, mesylate and tosylate ion.

Even more preferably, the leaving group X is selected from halogen, a $C_1$-$C_4$-alkyl sulfonate, a $C_6$-$C_{20}$-aryl sulfonate and an ammonium group of the formula (VI) wherein $R_1$, $R_2$ and $R_3$ are each independently selected from $C_1$-$C_6$-alkyl and $Y^-$ is selected from a halide ion (preferably a chloride ion).

Still more preferably, the leaving group X is selected from chlorine, bromine, iodine, mesylate, tosylate, a trimethyl ammonium chloride group of the formula (VIa)

—N(CH$_3$)$_3$$^+$Cl$^-$ (VIa), and a triethyl ammonium chloride group of the formula (VIb)

—N(CH$_2$CH$_3$)$_3$$^+$Cl$^-$ (VIb).

Yet more preferably, the leaving group X is selected from chlorine, bromine, iodine, mesylate, tosylate and a trimethyl ammonium chloride group of the formula (VIa).

Still even more preferably, the leaving group X is selected from chlorine, mesylate, tosylate and a trimethyl ammonium chloride group of the formula (VIa).

In another preferred embodiment, the leaving group X is selected from halogen, in particular from chlorine, bromine and iodine. Most preferably, the leaving group X is chlorine.

In yet another embodiment, the 2-Methylbenzyl compound of the formula (V) is selected from the group consisting of 2-Methylbenzyl chloride (1-(chloromethyl)-2-methyl-benzene) of the formula (Va)

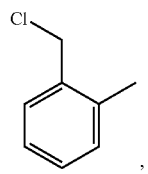

(Va)

,

2-Methylbenzyl bromide (1-(bromomethyl)-2-methyl-benzene) of the formula (Vb)

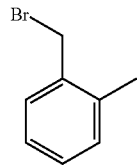

(Vb)

,

2-Methylbenzyl iodide (1-(iodomethyl)-2-methyl-benzene) of the formula (IIIc)

(Vc)

,

2-Methylbenzyl mesylate ((2-Methylphenyl)methyl methanesulfonate) of the formula (Vd)

(Vd)

,

2-Methylbenzyl tosylate ((2-methylphenyl)methyl 4-methylbenzenesulfonate) of the formula (Ve)

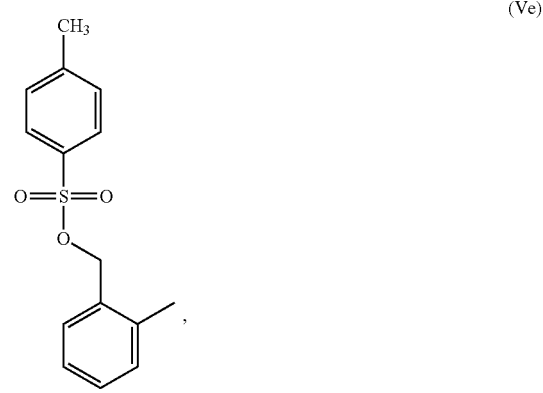 [SMILES: Cc1ccc(S(=O)(=O)OCc2ccccc2C)cc1]

(Ve)

,

Trimethyl(o-tolylmethyl)ammonium chloride of the formula (Vf)

(Vf)

and

Triethyl(o-tolylmethyl)ammonium chloride of the formula (Vg)

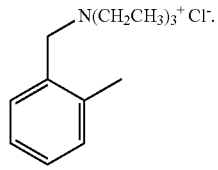

(Vg)

Most preferably, the 2-Methylbenzyl compound of the formula (V) is 2-Methylbenzyl chloride (1-(chloromethyl)-2-methyl-benzene) of the formula (Va).

The 2-Methylbenzyl compound of the formula (V) used as a starting material in the process or method of this invention is either commercially available or can be prepared by methods known in the art or in an analogous manner.

For example, a 2-Methylbenzyl compound of the formula (V) wherein X is halogen (such as e.g. 2-Methylbenzyl chloride of the formula (Va)) may be prepared by the method described in Synthetic Communications, Volume 33, Issue 7, pages 1103-1107, 2003 or in an analogous manner.

For example, the 2-Methylbenzyl compound of the formula (V) wherein X is a $C_1$-$C_4$-alkyl sulfonate or $C_6$-$C_{20}$-aryl sulfonate (such as e.g. 2-Methylbenzyl mesylate of the formula (Vd) or 2-Methylbenzyl tosylate of the formula (Ve)) may be prepared by methods described in Energy & Fuels, 21(3), pages 1695-1698, 2007 or Phosphorus, Sulfur and Silicon and the Related Elements, 184(5), pages 1161-1174, 2009.

The 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)) may be prepared by methods analogous to those described in Organic Syntheses, Coll. Vol. 4, p. 98 (1963); Vol. 38, p. 5 (1958). For example, the 2-Methylbenzyl compound of the formula (V) wherein X is selected from halogen (preferably chlorine, bromine or iodine and more preferably chlorine), a $C_1$-$C_4$-alkyl sulfonate (preferably mesylate) or a $C_6$-$C_{20}$-aryl sulfonate (preferably tosylate) is reacted with a tertiary amine of the formula $NR_1R_2R_3$ wherein $R_1$, $R_2$ and $R_3$ have the same meaning as in formula (VI) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) in a suitable solvent such as e.g. anhydrous ethanol.

The 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)) can be added to the reaction mixture separately (i.e. as isolated substance or in solution of any suitable solvent), or formed in the reaction mixture in-situ.

When the in-situ formation of the 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)) is desired, the step (b) or both steps (a) and (b) are conducted in the presence of at least one tertiary amine of the formula $NR_1R_2R_3$ wherein $R_1$, $R_2$ and $R_3$ have the same meaning as in formula (VI) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl).

In particular, the 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)) may be formed in-situ by reacting the 2-Methylbenzyl compound of the formula (V) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) with a tertiary amine of the formula $NR_1R_2R_3$ wherein $R_1$, $R_2$ and $R_3$ have the same meaning as in formula (VI) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) in the process of this invention.

For this purpose, the tertiary amine of the formula $NR_1R_2R_3$, can be added to step (a), step (b) or both steps (a) and (b). When both steps (a) and (b) are conducted in the presence of at least one tertiary amine of the formula $NR_1R_2R_3$, said tertiary amine may only be added to step (a), i.e. without further addition to step (b), so that the unreacted tertiary amine can still be used in step (b). Alternatively, said tertiary amine may also be added to both steps (a) and (b). For example, one amount of said tertiary amine is added to step (a) and a second amount of said tertiary amine is added to step (b).

Examples of suitable tertiary amines of the formula $NR_1R_2R_3$ are tri-($C_1$-$C_6$)-alkylamines such as trimethylamine, triethylamine, tributylamine and N,N-diisopropylethylamine; di-($C_1$-$C_6$)-alkyl-phenylamines such as N,N-dimethylaniline and N,N-diethylaniline; and the like.

Preferably, a tertiary amine of the formula $NR_1R_2R_3$ is used wherein $R_1$, $R_2$ and $R_3$ are each $C_1$-$C_6$-alkyl, more preferably $C_1$-$C_4$-alkyl, in particular methyl or ethyl and most preferably methyl.

Thus, in an especially preferred embodiment, the tertiary amine of the formula $NR_1R_2R_3$ is selected from trimethylamine, triethylamine or a combination thereof. Most preferably, the tertiary amine of the formula $NR_1R_2R_3$ is trimethylamine.

It is envisioned that the tertiary amine $NR_1R_2R_3$ replaces the leaving group X in the 2-Methylbenzyl compound of the formula (V) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) to form the respective ammonium-salt, i.e. the 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)). The ammonium salt formed in-situ immediately reacts with the metal alkoxide or metal alkoxide solvate of the formula (IV), any of its individual enantiomers or any non-racemic mixture thereof being present in the reaction mixture. During this benzylation, the tertiary amine is released again and thus available for restarting the nucleophilic substitution of the 2-Methylbenzyl compound of the formula (V) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine).

The aforementioned in-situ formation of the 2-Methylbenzyl compound of the formula (V) wherein X is an ammonium group of the formula (VI) is further illustrated in the following reaction scheme.

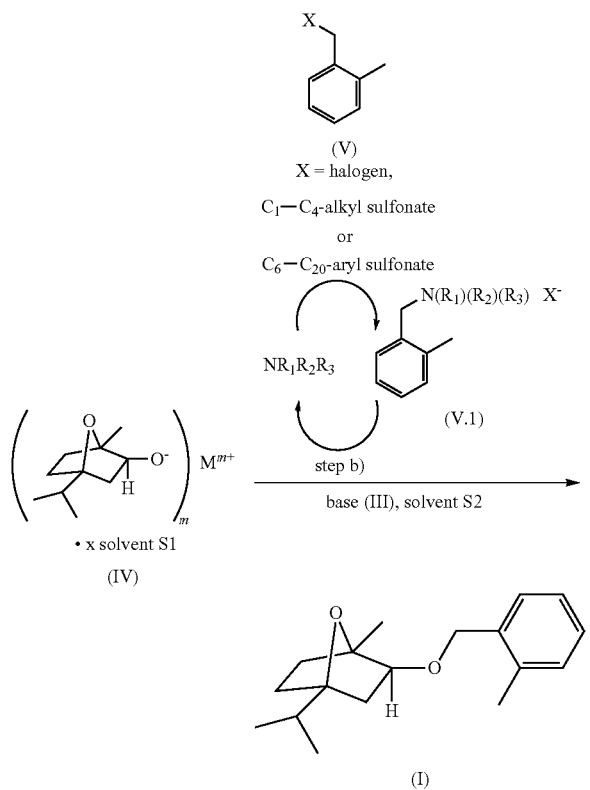

Hence, this variant of the process or method according to the invention is particularly advantageous because only substoichiometric or even catalytic amounts of the tertiary amine $NR_1R_2R_3$ relative to the 2-Methylbenzyl compound of the formula (V) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) are required without discontinuing the benzylation reaction. Moreover, the higher electrophilicity due to the ionic nature of the 2-Methylbenzyl compound of the formula (V) wherein X is an ammonium group of the formula (VI) leads to an acceleration of the reaction as compared to directly using the 2-Methylbenzyl compound of the formula (V) wherein X is selected from halogen, a $C_1$-$C_4$-alkyl sulfonate or a $C_6$-$C_{20}$-aryl sulfonate as the electrophilic reagent. Further, the amphiphilic character of the 2-Methylbenzyl compound of the formula (V) wherein X is an ammonium group of the formula (VI) is also beneficial given that the reaction medium forms a heterogeneous mixture comprising a liquid and solid phase.

The molar ratio of the 2-Methylbenzyl compound of the formula (V) (in particular 2-Methylbenzyl chloride of the formula (Va)) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the nature of the 2-Methylbenzyl compound (V) employed and the reaction conditions used, but is generally from 3:1 to 0.9:1, preferably from 2:1 to 0.9:1, more preferably from 1.5:1 to 0.9:1 and even more preferably from 1.1:1 to 0.9:1.

In step (a) of the process or method of this invention, (±)-2-exo-hydroxy-1-methyl-4-isopropyl-7-oxabicyclo[2.2.1]heptane of the formula (II), any one of its individual enantiomers or any non-racemic mixture thereof is deprotonated in the presence of at least one base of the formula $[M^{m+}]_n [A^{n-}]_m$ (III) wherein $M^{m+}$ represents a m-valent metal cation wherein m is an integer of 1 or 2, and $A^{n-}$ represents a n-valent anion wherein n is an integer of 1 or 2, said base being capable of forming water, a $C_1$-$C_4$-alkyl alcohol or any combination thereof under the reaction conditions, to form a metal alkoxide or metal alkoxide solvate of the formula (IV).

Preferably, m is an integer of 1. In another preferred embodiment, n is an integer of 1. In another embodiment, m is an integer of 1 and n is an integer of 1 or 2, preferably 1.

In the base of the formula (III), the m-valent cation $M^{m+}$ is preferably an alkali metal cation or alkaline earth metal cation, more preferably an alkali metal cation. The n-valent anion $A^{n-}$ is preferably hydroxide ($OH^-$), carbonate ($CO_3^{2-}$), hydrogen carbonate ($HCO_3^-$), oxide ($O^{2-}$) or $C_1$-$C_4$-alkoxide ($C_1$-$C_4$-alkyl-$O^-$), more preferably hydroxide, carbonate or $C_1$-$C_4$-alkoxide, even more preferably hydroxide or $C_1$-$C_4$-alkoxide and most preferably hydroxide.

In another embodiment, the m-valent cation $M^{m+}$ is an alkali metal cation or alkaline earth metal cation and the n-valent anion $A^{n-}$ is hydroxide, carbonate, hydrogen carbonate, oxide or $C_1$-$C_4$-alkoxide. Preferably, the m-valent cation $M^{m+}$ is an alkali metal cation and the n-valent anion $A^{n-}$ is hydroxide, carbonate, hydrogen carbonate, oxide or $C_1$-$C_4$-alkoxide. More preferably, the m-valent cation $M^{m+}$ is an alkali metal cation and the n-valent anion $A^{n-}$ is hydroxide or $C_1$-$C_4$-alkoxide. Even more preferably, the m-valent cation $M^{m+}$ is an alkali metal cation and the n-valent anion $A^{n-}$ is hydroxide.

The term "alkali metal" as used herein includes e.g. lithium, sodium and potassium.

The term "alkaline earth metal" as used herein includes e.g. calcium, magnesium and barium.

In a preferred embodiment, the m-valent cation $M^{m+}$ is $Li^+$, $Na^+$, $K^+$, $Mg^{2+}$, $Ca^{2+}$ or $Ba^{2+}$, more preferably $Li^+$, $Na^+$ or $K^+$, even more preferably $Na^+$ or $K^+$ and most preferably $Na^+$.

In another preferred embodiment, the n-valent anion $A^{n-}$ is hydroxide, carbonate, hydrogen carbonate, oxide, methoxide ($CH_3O^-$), ethoxide ($CH_3CH_2O^-$), n-propoxide ($CH_3(CH_2)_2O^-$), iso-propoxide (($CH_3)_2CHO^-$), n-butoxide ($CH_3(CH_2)_3O^-$) or tert-butoxide (($CH_3)_3CO^-$), more preferably hydroxide, carbonate or methoxide ($CH_3O^-$), even more preferably hydroxide or methoxide ($CH_3O^-$) and most preferably hydroxide.

In particular, the base (III) is selected from alkali metal and alkaline earth metal hydroxides, alkali metal and alkaline earth metal carbonates, alkali metal and alkaline earth metal hydrogen carbonates, alkali metal and alkaline earth metal oxides, alkali metal and alkaline earth metal $C_1$-$C_4$-alkoxides and any combination thereof, more preferably from alkali metal and alkaline earth metal hydroxides, alkali metal and alkaline earth metal carbonates, alkali metal and alkaline earth metal $C_1$-$C_4$-alkoxides and any combination thereof, even more preferably from alkali metal hydroxides, alkali metal carbonates, alkali metal $C_1$-$C_4$-alkoxides and any combination thereof, yet more preferably from alkali metal hydroxides, alkali metal $C_1$-$C_4$-alkoxides and any combination thereof, and still more preferably from alkali metal hydroxides.

As alkali metal hydroxides, there can be used lithium hydroxide, sodium hydroxide and potassium hydroxide.

As alkaline earth metal hydroxides, there can be used calcium hydroxide, magnesium hydroxide or barium hydroxide.

As alkali metal carbonates, there can be used lithium carbonate, sodium carbonate or potassium carbonate.

As alkaline earth metal carbonates, there can be used calcium carbonate, magnesium carbonate or barium carbonate.

As alkali metal hydrogen carbonates, there can be used lithium hydrogen carbonate, sodium hydrogen carbonate or potassium hydrogen carbonate.

As alkaline earth metal hydrogen carbonates, there can be used calcium hydrogen carbonate, magnesium hydrogen carbonate or barium hydrogen carbonate.

As alkali metal oxides, there can be used lithium oxide, sodium oxide or potassium oxide.

As alkaline earth metal oxides, there can be used calcium oxide, magnesium oxide or barium oxide.

As alkali metal $C_1$-$C_4$-alkoxides there can be used lithium methoxide, sodium methoxide, potassium methoxide, lithium ethoxide, sodium ethoxide, potassium ethoxide, lithium n-propoxide, sodium n-propoxide, potassium n-propoxide, lithium iso-propoxide, sodium iso-propoxide, potassium iso-propoxide, lithium n-butoxide, sodium n-butoxide, potassium n-butoxide, lithium tert-butoxide, sodium tert-butoxide or potassium tert-butoxide.

As alkaline earth metal $C_1$-$C_4$-alkoxides, there can be used magnesium dimethoxide, calcium dimethoxide, barium dimethoxide, magnesium diethoxide, calcium diethoxide, barium diethoxide, magnesium di-n-propoxide, calcium di-n-propoxide, barium di-n-propoxide, magnesium di-iso-propoxide, calcium di-iso-propoxide, barium di-iso-propoxide, magnesium di-n-butoxide, calcium di-n-butoxide, barium di-n-butoxide, magnesium di-tert-butoxide, calcium di-tert-butoxide or barium di-tert-butoxide.

In a preferred embodiment, the base (III) is selected from lithium hydroxide, sodium hydroxide, potassium hydroxide, calcium hydroxide, magnesium hydroxide, barium hydroxide, lithium carbonate, sodium carbonate, potassium carbonate, calcium carbonate, magnesium carbonate, barium carbonate, lithium hydrogen carbonate, sodium hydrogen carbonate, potassium hydrogen carbonate, calcium hydrogen carbonate, magnesium hydrogen carbonate, barium hydrogen carbonate, lithium oxide, sodium oxide, potassium oxide, calcium oxide, magnesium oxide, barium oxide, lithium methoxide, sodium methoxide, potassium methoxide, lithium ethoxide, sodium ethoxide, potassium ethoxide, lithium n-propoxide, sodium n-propoxide, potassium n-propoxide, lithium iso-propoxide, sodium iso-propoxide, potassium iso-propoxide, lithium n-butoxide, sodium n-butoxide, potassium n-butoxide, lithium tert-butoxide, sodium tert-butoxide, potassium tert-butoxide, magnesium dimethoxide, calcium dimethoxide, barium dimethoxide, magnesium diethoxide, calcium diethoxide, barium diethoxide, magnesium di-n-propoxide, calcium di-n-propoxide, barium di-n-propoxide, magnesium di-iso-propoxide, calcium di-iso-propoxide, barium di-iso-propoxide, magnesium di-n-butoxide, calcium di-n-butoxide, barium di-n-butoxide, magnesium di-tert-butoxide, calcium di-tert-butoxide, barium di-tert-butoxide and any combination thereof, more preferably from lithium hydroxide, sodium hydroxide, potassium hydroxide, calcium hydroxide, magnesium hydroxide, barium hydroxide, lithium carbonate, sodium carbonate, potassium carbonate, calcium carbonate, magnesium carbonate, barium carbonate, lithium methoxide, sodium methoxide, potassium methoxide, magnesium dimethoxide, calcium dimethoxide, barium dimethoxide and any combination thereof, even more preferably from lithium hydroxide, sodium hydroxide, potassium hydroxide, lithium carbonate, sodium carbonate, potassium carbonate, lithium methoxide, sodium methoxide, potassium methoxide and any combination thereof, still more preferably from lithium hydroxide, sodium hydroxide, potassium hydroxide, lithium methoxide, sodium methoxide, potassium methoxide and any combination thereof, yet more preferably from sodium hydroxide, potassium hydroxide, sodium methoxide, potassium methoxide and any combination thereof and still even more preferably from sodium hydroxide, potassium hydroxide and a combination thereof. Most preferably, the base (III) is sodium hydroxide.

In accordance with the invention, the base (III) is capable of forming a solvent S1 selected from water, a $C_1$-$C_4$-alkyl alcohol or any combination thereof under the reaction conditions.

Examples of $C_1$-$C_4$-alkyl alcohols include methanol, ethanol, n-propanol, iso-propanol (propan-2-ol), n-butanol, sec-butanol (butan-2-ol), iso-butanol (2-methyl-1-propanol), tert-butanol (2-methyl-2-propanol) or any combination thereof, preferably methanol, ethanol, iso-propanol, tert-butanol or any combination thereof and more preferably methanol.

In a preferred embodiment, the base (III) is capable of forming a solvent S1 selected from water, methanol, ethanol, iso-propanol, tert-butanol or any combination thereof (more preferably water, methanol or a combination thereof and most preferably water) under the reaction conditions.

In the metal alkoxide or metal alkoxide solvate of the formula (IV) formed in step (a), the variables $M^{m+}$, m and x, and the term "$C_1$-$C_4$-alkyl alcohol", independently of one another, have the following preferred meanings:

$M^{m+}$ is $Li^+$, $Na^+$, $K^+$, $Mg^{2+}$, $Ca^{2+}$ or $Ba^{2+}$, more preferably $Li^+$, $Na^+$ or $K^+$, even more preferably $Na^+$ or $K^+$ and most preferably $Na^+$;

m is 1;

x denotes a number from 0 to 10, more preferably from 0 to 5, even more preferably from 0 to 2 and still more preferably from 0 to 1;

the $C_1$-$C_4$-alkyl alcohol is selected from methanol, ethanol, n-propanol, iso-propanol (propan-2-ol), n-butanol, sec-butanol (butan-2-ol), iso-butanol (2-methyl-1-propanol) or tert-butanol (2-methyl-2-propanol) and any combination thereof, more preferably from methanol, ethanol, iso-propanol, tert-butanol and any combination thereof and even more preferably is methanol.

In another embodiment, $M^{m+}$ is $Na^+$ or $K^+$ (in particular $Na^+$), m is 1, the solvent S1 is water and x denotes a number from 0 to 1.

In yet another embodiment, $M^{m+}$ is $Na^+$ or $K^+$ (in particular $Na^+$), m is 1, the solvent S1 is selected from methanol, ethanol, iso-propanol, tert-butanol and any combination thereof (is preferably methanol) and x denotes a number from 0 to 1.

Further preferred metal alkoxides or metal alkoxide solvates of the formula (IV) are selected from the group consisting of

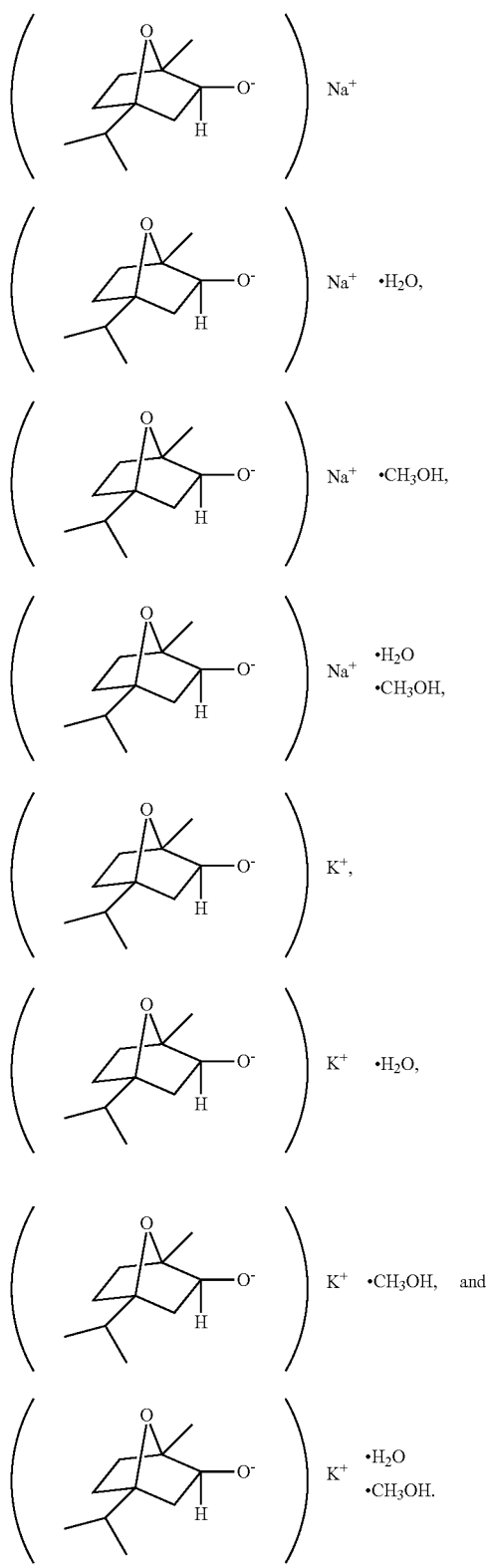

In step (a), the molar ratio of the base (III) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the reaction conditions used, but is generally from 1:1 to 5:1, preferably from 1:1 to 3:1, more preferably from 1:1 to 2:1 and even more preferably from 1:1 to 1.5:1.

The base (III) can be added to the reaction mixture in solid form, as an aqueous solution or as a combination thereof.

The term "solid form" as used herein includes but is not limited to powders, tablets, pellets, flakes, granules or micropearls.

The concentration of the base (III) in the aqueous solution can vary and depends on the nature of the base (III) and the reaction conditions used, but is generally from 5 to 50% by weight, preferably 10 to 50% by weight and more preferably 30 to 50% by weight of the base (III), based on the weight of the aqueous solution.

In one embodiment, the base (III) selected from alkali metal hydroxides (preferably from lithium hydroxide, sodium hydroxide, potassium hydroxide and any combination thereof, more preferably from sodium hydroxide, potassium hydroxide and a combination thereof and most preferably sodium hydroxide) is added to the reaction mixture (in particular in step (a)) in solid form. As solid forms of alkali metal hydroxides, there can be used pellets, flakes, granules or micropearls, preferably micropearls. The aforementioned solid forms of alkali metal hydroxides are commercially available from various suppliers. In another embodiment, the process of this invention (in particular step (a)) is conducted in the presence of sodium hydroxide micropearls as the base (III). In yet another embodiment, the base (III) preferably comprises sodium hydroxide micropearls and more preferably consists of sodium hydroxide micropearls.

In still another embodiment, the base (III) selected from alkali metal hydroxides (preferably from lithium hydroxide, sodium hydroxide, potassium hydroxide and any combination thereof, more preferably from sodium hydroxide, potassium hydroxide and a combination thereof and most preferably sodium hydroxide) is added to the reaction mixture (in particular in step (a)) as an aqueous solution. Preferably, the aqueous solution of the alkali metal hydroxide (preferably sodium hydroxide or potassium hydroxide and more preferably sodium hydroxide) comprises from 10 to 50% by weight, more preferably 25 to 50% by weight and even more preferably 35 to 50% by weight of the alkali metal hydroxide (preferably sodium hydroxide or potassium hydroxide and more preferably sodium hydroxide), based on the weight of the aqueous solution. Aqueous solutions of alkali metal hydroxides (preferably sodium hydroxide or potassium hydroxide and more preferably sodium hydroxide) can be provided by known methods but are also commercially available at a number of different concentrations.

The steps (a) and (b) of the process or method of this invention are conducted in the presence of at least one inert organic solvent S2.

In a preferred embodiment, the steps (a) and (b) are conducted in the same inert organic solvent S2. However, in another embodiment, steps (a) and (b) may be conducted in different inert organic solvents S2 as defined herein.

By the term "inert organic solvent" is meant an organic solvent which, under the reaction conditions of the process or method of this invention, does not enter into any appreciable reaction with either the reactants or the products.

The inert organic solvent S2 used in the process or method of this invention can be selected from a wide variety of solvents depending upon the reaction conditions used.

Suitable inert organic solvents S2 can be selected from hydrocarbons, amides, ethers, ketones, nitriles and any combination thereof.

The hydrocarbon used as the inert organic solvent S2 in this invention may be selected from aliphatic hydrocarbons, cycloaliphatic hydrocarbons, aromatic hydrocarbons, halogenated aliphatic hydrocarbons, halogenated aromatic hydrocarbons and any combination thereof.

Preferably, the inert organic solvent S2 can be selected from aliphatic hydrocarbons, cycloaliphatic hydrocarbons, aromatic hydrocarbons, halogenated aliphatic hydrocarbons, halogenated aromatic hydrocarbons, amides, ethers, ketones, nitriles and any combination thereof.

The term "aliphatic hydrocarbons" includes straight and branched chain aliphatic hydrocarbons.

Straight chain aliphatic hydrocarbons that can be used in the present invention are those having from 5 to 15 carbon atoms, preferably 5 to 10 carbon atoms. Examples of straight chain aliphatic hydrocarbons include n-pentane, n-hexane, n-heptane, n-octane, n-nonane, n-decane or any combination thereof, preferably n-heptane, n-octane, n-nonane, n-decane or any combination thereof.

The branched chain aliphatic hydrocarbons which are suitable for use in the present invention are those having from 4 to 15 carbon atoms, preferably 5 to 12 carbon atoms, more preferably 7 to 12 carbon atoms and even more preferably 8 to 11 carbon atoms. Examples of suitable branched chain aliphatic hydrocarbons include 2-methylpropane, 2-methylbutane, 2,3-dimethylbutane, 2-methylpentane, 3-methylpentane, 2,2-dimethylpentane, 2,3-dimethylpentane, 2,4-dimethylpentane, 2,2,4-trimethylpentane, 2-methylhexane, 3-methylhexane, 2,4-dimethylhexane, 2,5-dimethylhexane, 2,2,4-trimethylhexane, 2,3,4-trimethylhexane, 3,3,4-trimethylhexane, 2-methylheptane, 3-methylheptane, 2,3-dimethylheptane, 3,4-dimethylpentane, 2-ethyloctane, 2,3-dimethyloctane, 2-methylnonane, 3,4-dimethylnonane, 3-methyldecane, 2-methylundecane, 2-methyldodecane, 2,2,4 trimethyldodecane and any combination thereof.

Especially suitable are mixtures of branched chain aliphatic hydrocarbons having from 5 to 12 carbon atoms, preferably 7 to 12 carbon atoms and more preferably 8 to 11 carbon atoms, such as the commercial mixtures of isoparaffinic hydrocarbons sold under the tradename Isopar® by ExxonMobil Chemical, such as for example Isopar® E. Isopar E is a mixture of isoparaffinic hydrocarbons with a distillation range of 113° C. to 139° C.

Examples of suitable cycloaliphatic hydrocarbons include saturated or unsaturated cycloaliphatic hydrocarbons, such as e.g. cyclopentane, cyclohexane, cyclohexene, cycloheptane, cyclooctane, cyclooctene, 1,5-cyclooctadiene and the like. Preference is given to saturated cycloaliphatic hydrocarbons having from 5 to 10 carbon atoms. Cyclohexane is particularly preferred.

Examples of suitable aromatic hydrocarbons include toluene, o-xylene, m-xylene, p-xylene, ethylbenzene, 2-propylbenzene (cumene), 2-isopropyltoluene (o-cymol), 3-isopropyltoluene (m-cymol), 4-isopropyltoluene (p-cymol), 1,3,5-trimethylbenzene (mesitylene) and the like. Preference is given to toluene, o-xylene, m-xylene, p-xylene, ethylbenzene, 1,3,5-trimethylbenzene (mesitylene) and any combination thereof. Especially preferred among the aromatic hydrocarbons are toluene, o-xylene, m-xylene, p-xylene, 1,3,5-trimethylbenzene (mesitylene) and any combination thereof, with toluene being the most preferred.

Examples of suitable halogenated aliphatic hydrocarbons include methylene chloride, chloroform, carbon tetrachloride, 1,2-dichloroethane, 1,1,1,2-tetrachloroethane, 1,1,2,2-tetrachloroethane, 1,1-dichloroethylene, 1,2-dichloroethylene, and the like. Preference is given to methylene chloride and 1,2-dichloroethane and any combination thereof.

Examples of suitable halogenated aromatic hydrocarbons include chlorobenzene, bromobenzene, o-dichlorobenzene, m-dichlorobenzene, α,α,α-trifluorotoluene (benzotrifluoride) and the like.

Examples of suitable amides include N,N-dimethylformamide, dimethylacetamide, diethylacetamide, and the like.

Examples of suitable ethers include acyclic, cyclic or aromatic ethers such as diethyl ether, diisopropyl ether, n-butyl methyl ether, isobutyl methyl ether, sec-butyl methyl ether, tert-butyl methyl ether, cyclopentyl methyl ether, tetrahydrofuran, 2-methyltetrahydrofuran, 1,4-dioxane, anisole and the like.

Examples of suitable ketones include acetone, methyl ethyl ketone, methyl isopropyl ketone, methyl isobutyl ketone, cyclopropyl methyl ketone and the like.

Examples of suitable nitriles include acetonitrile, benzonitrile, and the like.

In a preferred embodiment, the inert organic solvent S2 is selected from hydrocarbons, acyclic ethers, cyclic ethers, aromatic ethers and any combination thereof, more preferably from aliphatic hydrocarbons, cycloaliphatic hydrocarbons, aromatic hydrocarbons, halogenated aliphatic hydrocarbons, halogenated aromatic hydrocarbons, acyclic ethers, cyclic ethers, aromatic ethers and any combination thereof, even more preferably from aliphatic hydrocarbons, aromatic hydrocarbons, halogenated aliphatic hydrocarbons, halogenated aromatic hydrocarbons and any combination thereof, yet more preferably from aliphatic hydrocarbons, aromatic hydrocarbons and any combination thereof, and still more preferably from aromatic hydrocarbons.

In another preferred embodiment, the inert organic solvent S2 is selected from hydrocarbons.

In a more preferred embodiment, the inert organic solvent S2 is selected from n-heptane, n-octane, n-nonane, n-decane, toluene, o-xylene, m-xylene, p-xylene, ethylbenzene, 1,3,5-trimethylbenzene (mesitylene), methylene chloride, chlorobenzene and any combination thereof.

In an even more preferred embodiment, the inert organic solvent S2 is selected from n-heptane, n-octane, toluene, o-xylene, m-xylene, p-xylene, ethylbenzene, 1,3,5-trimethylbenzene (mesitylene), chlorobenzene and any combination thereof.

Still more preferably, the inert organic solvent S2 is selected from n-heptane, toluene, o-xylene, m-xylene, p-xylene and any combination thereof.

Particularly preferred inert organic solvents S2 are alkylbenzenes which are mono-, di-, or trialkylsubstituted with each alkyl group containing 1 to 3 carbon atoms, in particular those selected from toluene, o-xylene, m-xylene, p-xylene, ethylbenzene, 1,3,5-trimethylbenzene (mesitylene) and any combination thereof and still more preferably selected from toluene, o-xylene, m-xylene, p-xylene and any combination thereof. Most preferably, the inert organic solvent S2 is toluene.

In another embodiment, the inert organic solvent S2 is capable of forming an azeotrope with the solvent S1 selected from water, the $C_1$-$C_4$-alkyl alcohol or any combination thereof.

Preferably, the inert organic solvent S2 is capable of forming an azeotrope with water.

In another embodiment, the inert organic solvent S2 is capable of forming an azeotrope with the solvent S selected from $C_1$-$C_4$-alkyl alcohols (preferably from methanol, ethanol, iso-propanol and tert-butanol and more preferably methanol).

In yet another embodiment, the inert organic solvent S2 is capable of forming an azeotrope with the solvent S1 selected from water, methanol, ethanol, iso-propanol or tert-butanol, preferably water, methanol, ethanol or tert-butanol, more preferably water or methanol and most preferably water.

In another embodiment, the inert organic solvent S2 has a boiling point at atmospheric pressure (1 bar) of from 35 to 200° C., preferably from 90 to 165° C. and more preferably from 100 to 150° C.

The molar ratio of the inert organic solvent S2 to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), can vary widely and depends on the reaction conditions used, but is generally from 30:1 to 1:1, preferably 20:1 to 1:1, more preferably from 15:1 to 1:1, even more preferably from 10:1 to 1:1 and still more preferably from 5:1 to 1:1.

In another embodiment, the molar ratio of the inert organic solvent S2 selected from aromatic hydrocarbons (in particular toluene) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), is 20:1 to 1:1, preferably 16:1 to 1:1, more preferably 15:1 to 1:1, even more preferably 13:1 to 2:1, yet more preferably 11:1 to 2:1, still more preferably 9:1 to 2:1 and in particular 6:1 to 3:1.

In case the base (III) is sodium hydroxide, the molar ratio of the inert organic solvent S2 selected from aromatic hydrocarbons (in particular toluene) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), is preferably 9:1 to 2:1, more preferably 6:1 to 3:1.

In case the base (III) is potassium hydroxide, the molar ratio of the inert organic solvent S2 selected from aromatic hydrocarbons (in particular toluene) to (±)-2-exo-hydroxy-1-methyl-4-isopropyl-7-oxabicyclo[2.2.1]heptane of the formula (II), any one of its individual enantiomers or any non-racemic mixture thereof, in particular (±)-2-exo-hydroxy-1-methyl-4-isopropyl-7-oxabicyclo[2.2.1]heptane of the formula (II), is preferably 16:1 to 4:1, more preferably 12:1 to 6:1.

In another embodiment, the molar ratio of the inert organic solvent S2 (preferably selected from aromatic hydrocarbons, in particular toluene) to the base (III) (preferably selected from alkali metal hydroxides, more preferably selected from sodium hydroxide, potassium hydroxide or a combination thereof) is 20:1 to 1:1, preferably 16:1 to 1:1, more preferably 13:1 to 1:1, even more preferably 10:1 to 1:1, yet more preferably 9:1 to 2:1 and in particular 6:1 to 2:1.

In yet another embodiment, the molar ratio of the inert organic solvent S2 (preferably selected from aromatic hydrocarbons, in particular toluene) to sodium hydroxide used as the base (III) is preferably 7:1 to 1:1, more preferably 5:1 to 2:1.

In still another embodiment, the molar ratio of the inert organic solvent S2 (preferably selected from aromatic hydrocarbons, in particular toluene) to potassium hydroxide used as the base (III) is preferably 16:1 to 4:1, more preferably 12:1 to 6:1.

The aforementioned molar ratios of the inert organic solvent S2 to the base (III) have been found especially advantageous in that not only the yield of the final product of the formula (I) but also its purity with less by-products can be increased.

In another preferred embodiment of the process or method of this invention, the m-valent metal cation $M^{m+}$ is an alkali metal cation, the n-valent anion $[A^{n-}]_m$ is hydroxide, n and m are both 1, the solvent S1 is water and the inert organic solvent S2 is selected from aromatic hydrocarbons (more preferably from alkylbenzenes which are mono-, di-, or trialkylsubstituted with each alkyl group containing 1 to 3 carbon atoms, in particular from toluene, o-xylene, m-xylene, p-xylene, ethylbenzene, 1,3,5-trimethylbenzene (mesitylene) and any combination thereof and still more preferably from toluene, o-xylene, m-xylene, p-xylene and any combination thereof and is most preferably toluene).

In yet another preferred embodiment of the process or method of this invention, the m-valent metal cation $M^{m+}$ is $Na^+$ or $K^+$, the n-valent anion $[A^{n-}]_m$ is hydroxide, n and m are both 1, the solvent S1 is water and the inert organic solvent S2 is selected from aromatic hydrocarbons (more preferably from alkylbenzenes which are mono-, di-, or trialkylsubstituted with each alkyl group containing 1 to 3 carbon atoms, in particular from toluene, o-xylene, m-xylene, p-xylene, ethylbenzene, 1,3,5-trimethylbenzene (mesitylene) and any combination thereof and still more preferably from toluene, o-xylene, m-xylene, p-xylene and any combination thereof and is most preferably toluene).

In yet another preferred embodiment of the process or method of this invention, the m-valent metal cation $M^{m+}$ is $Na^+$, the n-valent anion $[A^{n-}]_m$ is hydroxide, n and m are both 1, the solvent S1 is water and the inert organic solvent S2 is selected from aromatic hydrocarbons (more preferably from alkylbenzenes which are mono-, di-, or trialkylsubstituted with each alkyl group containing 1 to 3 carbon atoms, in particular from toluene, o-xylene, m-xylene, p-xylene, ethylbenzene, 1,3,5-trimethylbenzene (mesitylene) and any combination thereof and still more preferably from toluene, o-xylene, m-xylene, p-xylene and any combination thereof and is most preferably toluene).

In yet another preferred embodiment of the process or method of this invention, the base of the formula $[M^{m+}]_n$ $[A^{n-}]_m$ (III) is selected from alkali metal hydroxides, the solvent S1 is water and the inert organic solvent S2 is selected from aromatic hydrocarbons (more preferably from alkylbenzenes which are mono-, di-, or trialkylsubstituted with each alkyl group containing 1 to 3 carbon atoms, in particular from toluene, o-xylene, m-xylene, p-xylene, ethylbenzene, 1,3,5-trimethylbenzene (mesitylene) and any combination thereof and still more preferably from toluene, o-xylene, m-xylene, p-xylene and any combination thereof and is most preferably toluene).

In yet another preferred embodiment of the process or method of this invention, the base of the formula $[M^{m+}]_n$ $[A^{n-}]_m$ (III) is selected from sodium hydroxide, potassium hydroxide or a combination thereof, the solvent S1 is water and the inert organic solvent S2 is selected from aromatic hydrocarbons (more preferably from alkylbenzenes which are mono-, di-, or trialkylsubstituted with each alkyl group containing 1 to 3 carbon atoms, in particular from toluene, o-xylene, m-xylene, p-xylene, ethylbenzene, 1,3,5-trimethylbenzene (mesitylene) and any combination thereof and still more preferably from toluene, o-xylene, m-xylene, p-xylene and any combination thereof and is most preferably toluene).

In yet another preferred embodiment of the process or method of this invention, the base of the formula $[M^{m+}]_n$ $[A^{n-}]_m$ (III) is sodium hydroxide, the solvent S1 is water and the inert organic solvent S2 is selected from aromatic hydrocarbons (more preferably from alkylbenzenes which are mono-, di-, or trialkylsubstituted with each alkyl group containing 1 to 3 carbon atoms, in particular from toluene, o-xylene, m-xylene, p-xylene, ethylbenzene, 1,3,5-trimethylbenzene (mesitylene) and any combination thereof and still more preferably from toluene, o-xylene, m-xylene, p-xylene and any combination thereof and is most preferably toluene).

The step (a) and/or step (b) of the process or method of the present invention may optionally be carried out in the presence of at least one phase-transfer catalyst.

Phase transfer catalysts suitable for use in the process or method of this invention are those well known in the art such as, for example, quaternary ammonium salts. Examples of suitable phase-transfer catalysts are trimethyl(phenyl)ammonium chloride, bromide, iodide or hydroxide and tetra-n-$C_1$-$C_{12}$-alkyl-ammonium chlorides, bromides, iodides or hydroxides, preferably tetra-n-$C_1$-$C_8$-alkyl-ammonium chlorides, bromides, iodides or hydroxides, e.g. tetramethylammonium chloride, bromide, iodide or hydroxide, tetraethylammonium chloride, bromide, iodide or hydroxide, tetra-n-propylammonium chloride, bromide, iodide or hydroxide, tetra-n-butylammonium chloride, bromide, iodide or hydroxide, tetra-n-pentylammonium chloride, bromide, iodide or hydroxide, tetra-n-hexylammonium chloride, bromide, iodide or hydroxide, tetra-n-heptylammonium chloride, bromide, iodide or hydroxide, tetra-n-octylammonium chloride, bromide, iodide or hydroxide, methyl-tri-n-butylammonium chloride, bromide, iodide or hydroxide, ethyl-tri-methylammonium chloride, bromide, iodide or hydroxide, n-propyl-trimethyl ammonium chloride, bromide, iodide or hydroxide, methyl-triethyl ammonium chloride, bromide, iodide or hydroxide and n-butyl-triethylammonium chloride, bromide, iodide or hydroxide. Of these, the use of tetra-n-$C_1$-$C_4$-alkyl-ammonium chlorides, bromides, iodides or hydroxides is preferred, in particular tetra-n-butylammonium chloride, bromide, iodide or hydroxide and methyl-tri-n-butylammonium chloride, bromide, iodide or hydroxide. The phase-transfer catalysts, which are usually solid in pure form, can be used as such or, preferably, in dissolved form. An effective amount of the phase-transfer catalyst may range from 0.001 to 0.5 molar equivalents, preferably 0.001 to 0.2 molar equivalents relative to (±)-2-exo-hydroxy-1-methyl-4-isopropyl-7-oxabicyclo[2.2.1]heptane (II), any one of its individual enantiomers or any non-racemic mixture thereof, in particular (±)-2-exo-hydroxy-1-methyl-4-isopropyl-7-oxabicyclo[2.2.1]heptane (II).

The process or method of this invention can be carried out under atmospheric pressure or under slightly elevated or reduced pressure. Typically, the atmospheric pressure is employed. In another embodiment, the process or method of this invention is conducted under reduced pressure, preferably in a range of from 0.01 to 10 bar and more preferably 0.1 to 6 bar.

It is preferred that steps (a) and (b) are conducted at the same pressure. However, in another embodiment, steps (a) and (b) may be conducted at different pressures selected from the ranges as defined hereinabove.

The temperature used in the process or method of this invention can vary widely and depends on a variety of factors such as, for example, the inert organic solvent S2 and the pressure used. Under atmospheric pressure (1 bar), the temperature is generally from 35 to 200° C., preferably from 70 to 170° C., more preferably from 80 to 150° C. and even more preferably from 110 to 135° C.

It is preferred that steps (a) and (b) are conducted at the same temperature. However, in another embodiment, steps (a) and (b) may be conducted at different temperatures selected from the ranges as defined hereinabove.

The reaction time can vary in a wide range and depends on a variety of factors such as, for example, temperature, pressure, or the reagents and auxiliary substances used. Typical reaction times are in the range of from 10 to 60 hours, preferably from 12 to 30 hours and more preferably from 15 to 25 hours.

In yet another embodiment, the step (a) comprises the steps of (a1.1) providing a first mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)), the base (III) and the inert organic solvent S2, and (a1.2) heating the first mixture to reflux to give a second mixture comprising the metal alkoxide or metal alkoxide solvate of the formula (IV), any of its individual enantiomers or any non-racemic mixture thereof.

In case the 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)) is formed in-situ as described herein, a preferred embodiment of the step (a) comprises the steps of (a2.1) providing a first mixture comprising (±)-2-exo-hydroxy-1-methyl-4-isopropyl-7-oxabicyclo[2.2.1]heptane of the formula (II), any of its individual enantiomers or any non-racemic mixture thereof (preferably (±)-2-exo-hydroxy-1-methyl-4-isopropyl-7-oxabicyclo[2.2.1]heptane of the formula (II)), the base (III), the inert organic solvent S2 and the tertiary amine of the formula $NR_1R_2R_3$ wherein $R_1$, $R_2$ and $R_3$ have the same meaning as in formula (VI) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl), and (a2.2) heating the first mixture to reflux to give a second mixture comprising the metal alkoxide or metal alkoxide solvate of the formula (IV), any of its individual enantiomers or any non-racemic mixture thereof.

In still another embodiment, the step (b) comprises the step of (b1) adding the 2-Methylbenzyl compound of the formula (V) to the second mixture obtained in step (a1.2) or (a2.2) under agitation to form the reaction mixture.

In case the 2-Methylbenzyl compound of the formula (V) wherein X is an ammonium group of the formula (VI) (such as e.g. trimethyl(o-tolylmethyl)ammonium chloride of the formula (Vf) or triethyl(o-tolylmethyl)ammonium chloride of the formula (Vg)) is formed in-situ as described herein, a preferred embodiment of the step (b) comprises the step of (b2) adding the 2-Methylbenzyl compound of the formula (V) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) and the tertiary amine of the formula $NR_1R_2R_3$ wherein $R_1$, $R_2$ and $R_3$ have the same meaning as in formula (VI) (preferably wherein $R_1$, $R_2$ and $R_3$ are each independently selected from $C_1$-$C_6$-alkyl and $C_6$-$C_{20}$-aryl, more preferably $C_1$-$C_6$-alkyl, even more preferably methyl or ethyl and most preferably methyl) to the second mixture obtained in step (a1.2) or (a2.2) under agitation to form the reaction mixture.

The molar ratio of the tertiary amine of the formula $NR_1R_2R_3$ (in particular trimethylamine, triethylamine or a combination thereof, more preferably trimethylamine) to the 2-Methylbenzyl compound of the formula (V) wherein X is selected from halogen, a $C_1$-$C_4$-alkyl sulfonate or a $C_6$-$C_{20}$-aryl sulfonate (preferably halogen, more preferably chlorine, bromine or iodine and even more preferably chlorine) may be from 1:1 to 0.1:1, preferably from 0.5:1 to 0.1:1, more preferably from 0.25:1 to 0.1:1, even more preferably from 0.15:1 to 0.1:1 and yet more preferably 0.1:1 to 0.01:1.

In step (a) and more specifically in step (a1.1) or step (a2.1) as defined hereinabove, the base (III) (in solid form, as an aqueous solution or as a combination thereof) can be added batch-wise (in one or more individual portions, preferably in one portion) or continuously metered in, with preference being given to the batch-wise addition.

In step (b) and more specifically in step (b1) or step (b2) as defined hereinabove, the 2-Methylbenzyl compound of the formula (V) can be added batch-wise (in one or more individual portions) or continuously metered in, with preference being given to the continuous metered addition.

In accordance with the invention, the steps (a) and (b) comprise the further step of (c) simultaneously removing the solvent S1 (preferably water, methanol or a mixture thereof and more preferably water) from the reaction mixture. In a preferred embodiment of further step (c), the solvent S1 (preferably water, methanol or a mixture thereof and more preferably water) is simultaneously and continuously or simultaneously and intermittently (more preferably simultaneously and continuously) removed from the reaction mixture during the reaction.

By "continuously removed" or "continuous removal" it is meant that the solvent S1 is substantially or completely continuously removed from the reaction mixture as the reaction progresses. In this regard, "continuous" or "continuously" are not meant in any way to exclude normal interruptions in the continuity of the removal step due to, for example, start-up of the process.

In further step (c), the removal of the solvent S1 (preferably water, methanol or a mixture thereof and more preferably water) can be achieved by various methods known in the art, such as, for example, chemical or physicochemical methods. As chemical methods, the addition of chemical scavengers or drying reagents (e.g. sodium sulfate, magnesium sulfate, molecular sieves, zeolites or calcium oxide) may be used. Physicochemical methods include but are not limited to membrane separation processes (e.g. nanofiltration) or azeotropic distillation. In a preferred embodiment, the solvent S1 (preferably water, methanol or a mixture thereof and more preferably water) is removed from the reaction mixture by azeotropic distillation. In particular, the solvent S1 (preferably water, methanol or a mixture thereof and more preferably water) is removed from the reaction mixture as an azeotrope formed by the inert organic solvent S2 and the solvent S1.

In order to balance the potential loss of the inert organic solvent S2 removed by the azeotropic distillation in the reaction mixture, fresh inert organic solvent S2, recycled inert organic solvent S2 or a mixture comprising the inert organic solvent S2 and having a lower concentration of the solvent S1 as compared to the azeotrope can be added to the reaction mixture during the reaction. Thus, in a preferred embodiment, the further step (c) comprises the steps of (c.1) simultaneously (preferably simultaneously and continuously) removing the solvent S1 as an azeotrope formed by the inert organic solvent S2 and the solvent S1, and (c.2) adding the inert organic solvent S2 or a mixture comprising the inert organic solvent S2 and having a lower concentration of the solvent S1 as compared to the azeotrope to the reaction mixture during the reaction.

In step (c.2) hereinabove, the inert organic solvent S2 (either fresh inert organic solvent S2, recycled inert organic solvent S2 or a combination thereof) or a mixture comprising the inert organic solvent S2 and having a lower concentration of the solvent S1 as compared to the azeotrope may be added to the reaction mixture continuously or periodically (preferably continuously) during the reaction.

The inert organic solvent S2 (either fresh inert organic solvent S2, recycled inert organic solvent S2 or a combination thereof) or a mixture comprising the inert organic solvent S2 and having a lower concentration of the solvent S1 as compared to the azeotrope may preferably added to the reaction mixture in an amount such that the initial volume of the reaction mixture or a volume which is less than the initial volume of the reaction mixture (e.g. ≤90% or ≤80% or ≤70% or ≤60% or ≤50% or ≤40% or ≤30% as compared to the initial volume of the reaction mixture) is maintained during the reaction. The inert organic solvent S2 (either fresh inert organic solvent S2, recycled inert organic solvent S2 or a combination thereof) or a mixture comprising the inert organic solvent S2 and having a lower concentration of the solvent S1 as compared to the azeotrope may also be added in an amount such that a volume which is higher than the initial volume of the reaction mixture is obtained.

In a preferred embodiment, further step (c) comprises the steps of (c3.1) distilling the azeotrope formed by the inert organic solvent S2 and water, (c3.2) continuously condensing and separating the azeotrope into an organic solvent phase and a water phase, (c3.3) recycling the organic solvent phase to the reaction mixture, and (c3.4) removing the water phase from the process.

In a particularly preferred embodiment, further step (c) comprises the steps of (c4.1) removing the azeotrope formed by the inert organic solvent S2 and water as a vapor fraction from the reaction mixture, (c4.2) condensing said vapor fraction to form a biphasic condensate and passing said biphasic condensate through a phase separator to form an organic solvent phase and a water phase, (c4.3) transferring the inert organic solvent phase (preferably via overflow) to the reaction mixture, and (c4.4) removing the water phase from the process.

(±)-2-exo-(2-Methylbenzyloxy)-1-methyl-4-isopropyl-7-oxabicyclo[2.2.1]heptane of the formula (I), any of its individual enantiomers or any non-racemic mixture thereof (preferably (±)-2-exo-(2-Methylbenzyloxy)-1-methyl-4-isopropyl-7-oxabicyclo[2.2.1]heptane of the formula (I)) is preferably isolated from the final reaction mixture obtained from step (b) by employing conventional methods, for example by extraction, in particular extraction with a basic or neutral aqueous medium, distillation, and the like.

After completion of the reaction, the reaction mixture is preferably extracted with water followed by concentration and removal of the inert organic solvent S2. For further purification, thin-film-evaporation as well as rectification can be applied.

The invention is illustrated by the following examples without being limited thereto or thereby.

EXAMPLE 1

Preparation of (±)-2-exo-(2-Methylbenzyloxy)-1-methyl-4-isopropyl-7-oxabicyclo[2.2.1]Heptane Using Removal of Water by Azeotropic Distillation (Base: Aqueous Solution of Sodium Hydroxide, Solvent: Toluene)

(±)-2-exo-hydroxy-1-methyl-4-isopropyl-7-oxabicyclo[2.2.1]heptane (102.2 g, 0.60 mol) was dissolved in toluene (165.9 g, 1.80 mol) and an aqueous solution of sodium hydroxide (50%) (62.4 g, 0.78 mol) was added. The mixture was heated to reflux (114-118° C.) and within 2 h water (25 g) was removed from the system (Dean-Stark conditions). 1-(chloromethyl)-2-methyl-benzene (140.6 g, 0.66 mol) was added within 1.5 h at 123° C. During dosage and reaction time water was continuously removed from the reaction mixture via azeotropic distillation. After 44 h the reaction mixture was cooled to room temperature. Water (160.0 g) was added and the reaction mixture was extracted. After phase separation a solution of sodium chloride (10%) (100.0 g) was added. After extraction the organic phase was separated and concentrated in vacuum. The product (169.4 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 91.7%. This corresponds to a yield of 94.4% of (±)-2-exo-(2-Methylbenzyloxy)-1-methyl-4-isopropyl-7-oxabicyclo[2.2.1]heptane.

EXAMPLE 2

Preparation of (±)-2-exo-(2-Methylbenzyloxy)-1-methyl-4-isopropyl-7-oxabicyclo[2.2.1]Heptane Using Removal of Methanol by Azeotropic Distillation (Base: Methanolic Solution of Sodium Methoxide and Solid Potassium Hydroxide, Solvent: Toluene)

(±)-2-exo-hydroxy-1-methyl-4-isopropyl-7-oxabicyclo[2.2.1]heptane (20.0 g, 0.12 mol) was dissolved in toluene (176.0 g, 1.91 mol). Sodium methoxide (30% in methanol) (23.3 g, 0.13 mol) and potassium hydroxide (85%) (0.7 g, 0.01 mol) were added. The suspension was heated to reflux and methanol/toluene-azeotrope was removed, while adding fresh toluene in order to keep the fluid level constant. Once the head temperature reached 110° C., distillation was stopped. 1-(chloromethyl)-2-methyl-benzene (18.2 g, 0.13 mol) was added within 10 min. The reaction mixture was stirred until full conversion of 1-(chloromethyl)-2-methyl-benzene. The reaction mixture was cooled to 25° C. and washed with water (70 g) and a solution of sodium chloride (15%) (70 g). The organic phase was concentrated in vacuum. The product (30.6 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 95.9%. This corresponds to a yield of 91.1% of (±)-2-exo-(2-Methylbenzyloxy)-1-methyl-4-isopropyl-7-oxabicyclo[2.2.1]heptane.

EXAMPLE 3

Preparation of (±)-2-exo-(2-Methylbenzyloxy)-1-methyl-4-isopropyl-7-oxabicyclo[2.2.1]Heptane Using Removal of Water by Azeotropic Distillation (Base: Aqueous Solution of Sodium Hydroxide, Solvent: Toluene)

(±)-2-exo-hydroxy-1-methyl-4-isopropyl-7-oxabicyclo[2.2.1]heptane (50.0 g, 0.29 mol) was dissolved in toluene (105.3 g, 1.14 mol) and an aqueous solution of sodium hydroxide (50%) (29.7 g, 0.37 mol) was added. The mixture was heated to reflux (110-113° C.) and within 2 h water (14.9 g) was removed from the system (Dean-Stark conditions). 1-(chloromethyl)-2-methyl-benzene (44.2 g, 0.31 mol) was added within 1 h at 112° C. During dosage and reaction time water was continuously removed from the reaction mixture via azeotropic distillation. After 32 h the reaction mixture was cooled to room temperature. Water (200.0 g) was added and the reaction mixture was extracted. After phase separation a solution of sodium chloride (10%) (60.0 g) was added. After extraction the organic phase was separated and concentrated in vacuum. The product (80.8 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 94.3%. This corresponds to a yield of 97.2% of (±)-2-exo-(2-Methylbenzyloxy)-1-methyl-4-isopropyl-7-oxabicyclo[2.2.1]heptane.

EXAMPLE 4

Preparation of (±)-2-exo-(2-Methylbenzyloxy)-1-methyl-4-isopropyl-7-oxabicyclo[2.2.1]Heptane Using Removal of Water by Azeotropic Distillation (Base: Aqueous Solution of Sodium Hydroxide, Solvent: Toluene)

(±)-2-exo-hydroxy-1-methyl-4-isopropyl-7-oxabicyclo[2.2.1]heptane (50.0 g, 0.29 mol) was dissolved in toluene (105.3 g, 1.14 mol) and an aqueous solution of sodium hydroxide (50%) (29.7 g, 0.37 mol) was added. The mixture was heated to reflux (110-113° C.) and within 2 h water (13.7 g) was removed from the system (Dean-Stark conditions). 1-(chloromethyl)-2-methyl-benzene (44.2 g, 0.31 mol) was added within 1 h at 112° C. During dosage and reaction time water was continuously removed from the reaction mixture via azeotropic distillation. After 32 h the reaction mixture was cooled to room temperature. Water (200.0 g) was added and the reaction mixture was extracted. After phase separation a solution of sodium chloride (10%) (60.0 g) was added. After extraction the organic phase was separated and concentrated in vacuum. The product (78.8 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 93.3%. This corresponds to a yield of 93.8% of (±)-2-exo-(2-Methylbenzyloxy)-1-methyl-4-isopropyl-7-oxabicyclo[2.2.1]heptane.

EXAMPLE 5

Preparation of (±)-2-exo-(2-Methylbenzyloxy)-1-methyl-4-isopropyl-7-oxabicyclo[2.2.1]Heptane Using Removal of Water by Azeotropic Distillation (Base: Aqueous Solution of Sodium Hydroxide, Solvent: Toluene)

(±)-2-exo-hydroxy-1-methyl-4-isopropyl-7-oxabicyclo[2.2.1]heptane (50.0 g, 0.29 mol) was dissolved in toluene (105.3 g, 1.14 mol) and an aqueous solution of sodium hydroxide (50%) (29.7 g, 0.37 mol) was added. The mixture was heated to reflux (110-113° C.) and within 2 h water (11.5 g) was removed from the system (Dean-Stark conditions). 1-(chloromethyl)-2-methyl-benzene (44.2 g, 0.31 mol) was added within 1 h at 112° C. During dosage and reaction time water was continuously removed from the reaction mixture via azeotropic distillation. After 42 h the reaction mixture was cooled to room temperature. Water (200.0 g) was added and the reaction mixture was extracted. After phase separation a solution of sodium chloride (10%) (60.0 g) was added. After extraction the organic phase was separated and concentrated in vacuum. The product (81.0 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 91.2%. This corresponds to a yield of 94.2% of (±)-2-exo-(2-Methylbenzyloxy)-1-methyl-4-isopropyl-7-oxabicyclo[2.2.1]heptane.

EXAMPLE 6

Preparation of (±)-2-exo-(2-Methylbenzyloxy)-1-methyl-4-isopropyl-7-oxabicyclo[2.2.1]Heptane Using Removal of Water by Azeotropic Distillation (Base: Solid Potassium Hydroxide, 1 Molar Equivalent; Solvent: Toluene, 6 Molar Equivalents)

(±)-2-exo-hydroxy-1-methyl-4-isopropyl-7-oxabicyclo[2.2.1]heptane (50.0 g, 0.29 mol) was dissolved in toluene (162.0 g, 1.76 mol). Potassium hydroxide (90%) (18.3 g, 0.29 mol) was added. The mixture was heated to reflux (110-113° C.) and within 1 h water (1.0 g) was removed from the system (Dean-Stark conditions). 1-(chloromethyl)-2-methyl-benzene (41.2 g, 0.29 mol) was added within 1 h at 113-117° C. During dosage and reaction time water was continuously removed from the reaction mixture via azeotropic distillation. After 5 h the reaction mixture was cooled to room temperature. Water (100.0 g) was added and the reaction mixture was extracted. After phase separation a solution of sodium chloride (10%) (60 ml) was added. After extraction the organic phase was separated and concentrated in vacuum. The product (80.3 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 94.7%. This corresponds to a yield of 94.5% of (±)-2-exo-(2-Methylbenzyloxy)-1-methyl-4-isopropyl-7-oxabicyclo[2.2.1]heptane.

EXAMPLE 7

Preparation of (±)-2-exo-(2-Methylbenzyloxy)-1-methyl-4-isopropyl-7-oxabicyclo[2.2.1]Heptane Using Removal of Water by Azeotropic Distillation (Base: Solid Potassium Hydroxide, 1.1 Molar Equivalents; Solvent: Toluene, 9 Molar Equivalents)

(±)-2-exo-hydroxy-1-methyl-4-isopropyl-7-oxabicyclo[2.2.1]heptane (375 g, 2.18 mol) was dissolved in toluene (1810.0 g, 19.65 mol). Potassium hydroxide (90%) (149.7 g, 2.40 mol) was added. The mixture was heated to reflux (108-110° C.) and within 2 h water (7.0 g) was removed from the system (Dean-Stark conditions). 1-(chloromethyl)-2-methyl-benzene (306.9 g, 2.18 mol) was added within 1 h at 113-115° C. During dosage and reaction time water (51.0 g) was continuously removed from the reaction mixture via azeotropic distillation. After 15 h the reaction mixture was cooled to room temperature. Water (500.0 g) was added and the reaction mixture was extracted. After phase separation a solution of sodium chloride (10%) (100 g) was added. After extraction the organic phase was separated and concentrated in vacuum. The product (609.0 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 90.0%. This corresponds to a yield of 91.5% of (±)-2-exo-(2-Methylbenzyloxy)-1-methyl-4-isopropyl-7-oxabicyclo[2.2.1]heptane.

EXAMPLE 8

Preparation of (±)-2-exo-(2-Methylbenzyloxy)-1-methyl-4-isopropyl-7-oxabicyclo[2.2.1]Heptane Using Removal of Water by Azeotropic Distillation (Base: Solid Potassium Hydroxide, 1.1 Molar Equivalents; Solvent: Toluene, 12 Molar Equivalents)

(±)-2-exo-hydroxy-1-methyl-4-isopropyl-7-oxabicyclo[2.2.1]heptane (50.0 g, 0.29 mol) was dissolved in toluene (324.0 g, 3.52 mol). Potassium hydroxide (90%) (56.1 g, 0.32 mol) was added. The mixture was heated to reflux (108-110° C.) and within 1 h water (1.0 g) was removed from the system (Dean-Stark conditions). 1-(chloromethyl)-2-methyl-benzene (41.2 g, 0.29 mol) was added within 1 h at 111-113° C. During dosage and reaction time water (51.0 g) was continuously removed from the reaction mixture via azeotropic distillation. After 13 h the reaction mixture was cooled to room temperature. Water (100.0 g) was added and the reaction mixture was extracted. After phase separation a solution of sodium chloride (10%) (60 ml) was added. After extraction the organic phase was separated and concentrated in vacuum. The product (80.7 g) was analyzed via quantitative high performance liquid chromatography (HPLC) and showed a (±)-2-exo-(2-Methylbenzyloxy)-1-methyl-4-isopropyl-7-oxabicyclo[2.2.1]heptane concentration of 90.6%. This corresponds to a yield of 90.9% of (±)-2-exo-(2-Methylbenzyloxy)-1-methyl-4-isopropyl-7-oxabicyclo[2.2.1]heptane.

COMPARISON EXAMPLE 1

Preparation of (±)-2-exo-(2-Methylbenzyloxy)-1-methyl-4-isopropyl-7-oxabicyclo[2.2.1]heptane Analogous to the preparation of cinmethylin metabolite 5 as described in Philip W. Lee et al., Journal of Agricultural and Food Chemistry, Vol. 34, No. 2, 1986, page 162

A solution of (±)-2-exo-hydroxy-1-methyl-4-isopropyl-7-oxabicyclo[2.2.1]heptane (23.8 g, 0.139 mol) in toluene (139.1 g, 1.510 mol) and powered sodium hydroxide (12.0 g, 0.291 mol) was refluxed under a Dean-Stark trap until no more water was removed. The solution was cooled to 25° C. and 1-(chloromethyl)-2-methyl-benzene (20.1 g, 0.143 mol) was added. The mixture was stirred at reflux for 24 h, cooled to room-temperature and washed with water (1x 104 g, 1×101 g). The organic phase was separated (115.9 g) and analyzed by quantitative gas chromatography and showed the desired (±)-2-exo-(2-Methylbenzyloxy)-1-methyl-4-isopropyl-7-oxabicyclo[2.2.1]heptane in 23.2 wt %. This corresponds to a yield of 70.4% of (±)-2-exo-(2-Methylbenzyloxy)-1-methyl-4-isopropyl-7-oxabicyclo[2.2.1]heptane.

COMPARISON EXAMPLE 2

Preparation of (±)-2-exo-(2-Methylbenzyloxy)-1-methyl-4-isopropyl-7-oxabicyclo[2.2.1]heptane According to CN 101602770 A, Pages 19-20, Example 3

(±)-2-exo-hydroxy-1-methyl-4-isopropyl-7-oxabicyclo[2.2.1]heptane (99.5%) (36.3 g, 0.21 mol) was dissolved in ethyl acetate (73.5 g, 0.83 mol) and sodium hydroxide (10.2 g, 0.25 mol) was added. 1-(chloromethyl)-2-methyl-benzene (38.6 g, 0.27 mol) was added dropwise within 1 h at ambient temperature. Then the mixture was heated to 50° C. and stirred for 5 h. The mixture was cooled to 25° C. and water (100 g) was added. After phase separation the organic phase was analyzed. The analysis showed less than 0.1% of the desired product (±)-2-exo-(2-Methylbenzyloxy)-1-methyl-4-isopropyl-7-oxabicyclo[2.2.1]heptane, but large amounts of the acetylation product 1 as shown in the formula below (16 area-%), (±)-2-exo-hydroxy-1-methyl-4-isopropyl-7-oxabicyclo[2.2.1]heptane (26 area-%), 1-(chloromethyl)-2-methyl-benzene (56 area-%), as well as resulting ethanol through acylation were identified by gaschromatography and GC-MS.

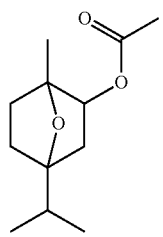

(1)

The invention claimed is:

1. A process for preparing (±)-2-exo-(2-Methylbenzyloxy)-1-methyl-4-isopropyl-7-oxabicyclo[2.2.1]heptane of the formula (I)

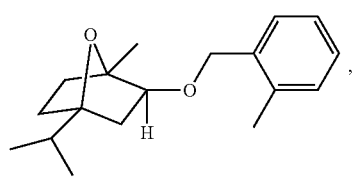

(I)

any one of its individual enantiomers or any non-racemic mixture thereof, the process comprising the steps of (a) deprotonating (±)-2-exo-hydroxy-1-methyl-4-isopropyl-7-oxabicyclo[2.2.1]heptane of the formula (II)

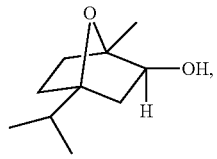

(II)

any one of its individual enantiomers or any non-racemic mixture thereof in the presence of at least one base of the formula $[M^{m+}]_n$, $[A^{n-}]_m$ (III) wherein $M^{m+}$ represents a m-valent metal cation which is an alkali metal cation wherein m is 1, and $A^{n-}$ represents a n-valent anion which is hydroxide wherein n is 1, said base being capable of forming a solvent S1 which is water under the reaction conditions, to form a metal alkoxide or metal alkoxide solvate of the formula (IV)

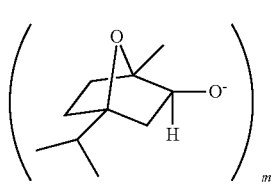

(IV)

any one of its individual enantiomers or any non-racemic mixture thereof wherein $M^{m+}$, m and the solvent S1 have the same meaning as defined for the base of formula (III), and x denotes a number from 0 to 10, and (b) reacting the metal alkoxide or metal alkoxide solvate of the formula (IV), any of its individual enantiomers or any non-racemic mixture thereof with a 2-Methylbenzyl compound of the formula (V)

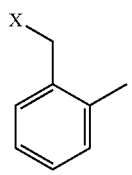

(V)

wherein X is a leaving group,
wherein the steps (a) and (b) are conducted in the presence of at least one inert organic solvent S2 selected from aromatic hydrocarbons and comprise a further step of
(c) simultaneously removing the solvent S1 from the reaction mixture.

2. The process according to claim 1 wherein, in further step (c), the solvent S1 is removed from the reaction mixture by azeotropic distillation.

3. The process according to claim 1 wherein the further step (c) comprises the steps of
(c.1) simultaneously removing the solvent S1 from the reaction mixture as an azeotrope formed by the inert organic solvent S2 and the solvent S1, and
(c.2) adding the inert organic solvent S2 or a mixture comprising the inert organic solvent S2 and having a lower concentration of the solvent S1 as compared to the azeotrope to the reaction mixture during the reaction.

4. The process according to claim 1 wherein, in the further step (c), the solvent S1 is simultaneously and continuously removed from the reaction mixture.

5. The process according to claim 1 wherein the base of the formula (III) is selected from the group consisting of sodium hydroxide, potassium hydroxide, and combinations thereof.

6. The process according to claim 1 wherein the base of the formula (III) is sodium hydroxide.

7. The process according to claim 1 wherein X is selected from halogen, an oxygen linked leaving group, and an ammonium group of the formula (VI)

  (VI)

wherein $R_1$, $R_2$ and $R_3$ are each independently selected from $C_1$-$C_6$-alkyl, $C_3$-$C_{10}$-cycloalkyl and $C_6$-$C_{20}$-aryl, and $Y^-$ is selected from halide, hydroxide, $C_1$-$C_4$-alkyl sulfonate and $C_6$-$C_{20}$-aryl sulfonate ions.

8. The process according to claim 1 wherein X is selected from halogen.

9. The process according to claim 1 wherein the inert organic solvent S2 is capable of forming an azeotrope with water.

10. The process according to claim 1 wherein the inert organic solvent S2 is selected from alkylbenzenes which are mono-, di-, or trialkylsubstituted with each alkyl group containing 1 to 3 carbon atoms.

11. The process according to claim 1 wherein the inert organic solvent S2 is toluene.

12. The process according to claim 1 wherein the 2-Methylbenzyl compound of the formula (V) is 2-Methylbenzyl chloride of the formula (Va)

  (Va)

13. A method for reducing the formation of deposits on the interior of a reactor in which the preparation of (±)-2-exo-(2-Methylbenzyloxy)-1-methyl-4-isopropyl-7-oxabicyclo[2.2.1]heptane of the formula (I)

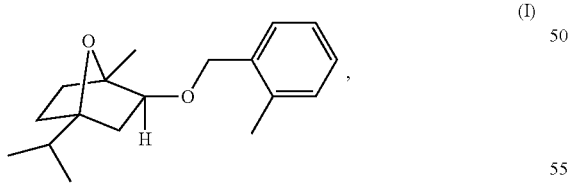  (I)

any one of its individual enantiomers or any non-racemic mixture thereof is conducted by benzylating (±)-2-exo-hydroxy-1-methyl-4-isopropyl-7-oxabicyclo[2.2.1]heptane of the formula (II)

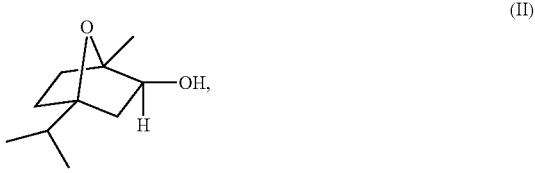  (II)

any one of its individual enantiomers or any non-racemic mixture thereof with a 2-methylbenzyl compound of the formula (V)

  (V)

wherein X is a leaving group, said method comprising the steps of (a) deprotonating (±)-2-exo-hydroxy-1-methyl-4-isopropyl-7-oxabicyclo[2.2.1]heptane of the formula (II), any one of its individual enantiomers or any non-racemic mixture thereof in the presence of at least one base of the formula $[M^{m+}]_n$ $[A^{n-}]_m$ (III) wherein $M^{m+}$ represents a m-valent metal cation which is an alkali metal cation wherein m is 1, and $A^{n-}$ represents a n-valent anion which is hydroxide wherein n is 1, said base being capable of forming a solvent S1 which is water under the reaction conditions, to form a metal alkoxide or metal alkoxide solvate of the formula (IV)

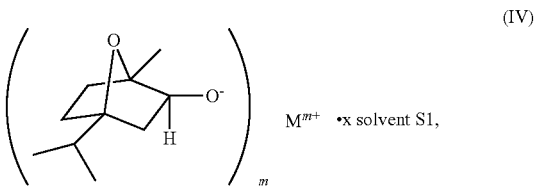  (IV)

any one of its individual enantiomers or any non-racemic mixture thereof wherein $M^{m+}$, m and the solvent S1 have the same meaning as defined for the base of formula (III), and x denotes a number from 0 to 10, and (b) reacting the metal alkoxide or metal alkoxide solvate of the formula (IV), any of its individual enantiomers or any non-racemic mixture thereof with the 2-Methylbenzyl compound of the formula (V)

wherein the steps (a) and (b) are conducted in the presence of at least one inert organic solvent S2 selected from aromatic hydrocarbons and comprise a further step of (c) simultaneously removing the solvent S1 from the reaction mixture.

* * * * *